United States Patent
Butruille et al.

(10) Patent No.: US 8,604,272 B2
(45) Date of Patent: Dec. 10, 2013

(54) RESISTANCE TO GRAY LEAF SPOT IN MAIZE

(75) Inventors: David Butruille, Des Moines, IA (US); Gilberto Pozar, Minas Gerais (BR)

(73) Assignee: Monsanto Technology LLC, St. Louis, MO (US)

( * ) Notice: Subject to any disclaimer, the term of this patent is extended or adjusted under 35 U.S.C. 154(b) by 902 days.

(21) Appl. No.: 12/443,162

(22) PCT Filed: Sep. 26, 2007

(86) PCT No.: PCT/US2007/020772
§ 371 (c)(1),
(2), (4) Date: Feb. 23, 2010

(87) PCT Pub. No.: WO2008/042185
PCT Pub. Date: Apr. 10, 2008

(65) Prior Publication Data
US 2010/0146657 A1    Jun. 10, 2010

Related U.S. Application Data

(60) Provisional application No. 60/847,659, filed on Sep. 28, 2006, provisional application No. 60/860,210, filed on Nov. 21, 2006.

(51) Int. Cl.
*A01H 1/04* (2006.01)
*C12N 15/10* (2006.01)
*C12N 15/29* (2006.01)

(52) U.S. Cl.
USPC ........ 800/265; 800/267; 800/320.1; 800/275; 435/6.12

(58) Field of Classification Search
None
See application file for complete search history.

(56) References Cited

U.S. PATENT DOCUMENTS

| | | | |
|---|---|---|---|
| 5,574,210 A | 11/1996 | Saghai-Maroof et al. | |
| 7,214,786 B2 * | 5/2007 | Kovalic et al. | 536/23.6 |
| 2004/0214272 A1* | 10/2004 | La Rosa et al. | 435/69.1 |
| 2006/0112465 A1 | 5/2006 | Hoffbeck | |

FOREIGN PATENT DOCUMENTS

CN    1443440 A    9/2003

OTHER PUBLICATIONS

Li et al., "Flow sorting and microcloning of maize chromosome 1," *Hereditas*, 141:55-60 (2004).
Messing et al., "Sequence composition and genome organization of maize," *PNAS*, 101(40):14349-14354 (2004).
Bubeck et al., "Quantitative trait loci controlling resistance to gray leaf spot in maize", *Crop Science* 33(4):838-847 (1993).
Clements et al., "Quantitative trait loci associated with resistance to gray leaf spot of corn", *Phytopathology* 90(9):1018-1025(2000).
Gordon et al., "Linkage of molecular markers to *Cercospora zeae-maydis* resistance in maize", *Crop Science* 44(2):628-636 (2004).
International Search Report mailed Aug. 14, 2008 in PCT/US2007/020772.
Lehmensiek et al., "Genetic mapping of gray leaf spot (GLS) resistance genes in maize," *Theoretical and Applied Genetics* 103(5):797-803 (2001).
Wisser et al., "The genetic architecture of disease resistance in maize: A synthesis of published studies," *Phytopathology* 96(2):120-129 (2006).
Davis et al., "A Maize Map Standard With Sequenced Core Markers, Grass Genome Reference Points and 932 Expressed Sequence Tagged Sites (ESTs) in a 1736-Locus Map," *Genetics*, 152:1137-1172 (1999).
Gardiner et al., "Development of a Core RFLP Map in Maize Using an Immortalized $F_2$ Population," *Genetics*, 134:917-930 (1993).

* cited by examiner

*Primary Examiner* — David T Fox
*Assistant Examiner* — Jared Shapiro
(74) *Attorney, Agent, or Firm* — Lawrence M. Lavin, Jr.; Arnold & Porter LLP

(57) ABSTRACT

The present invention is in the field of plant breeding and disease resistance. More specifically, the invention includes a method for breeding corn plants containing quantitative trait loci that are associated with resistance to gray leaf spot, a fungal disease associated with *Cercospora* spp. The invention further includes germplasm and the use of germplasm containing quantitative trait loci (QTL) conferring disease resistance for introgression into elite germplasm in a breeding program for resistance to gray leaf spot.

26 Claims, No Drawings

SEQUENCE LISTING

<160> NUMBER OF SEQ ID NOS: 78

<210> SEQ ID NO 1
<211> LENGTH: 708
<212> TYPE: DNA
<213> ORGANISM: Zea mays
<220> FEATURE:
<221> NAME/KEY: UNSURE
<222> LOCATION: (1)..(708)
<223> OTHER INFORMATION: n=A, T, C, or G
<220> FEATURE:
<221> NAME/KEY: unsure
<222> LOCATION: (1)..(708)
<223> OTHER INFORMATION: unsure at all n locations

<400> SEQUENCE: 1

```
tgcannatgg acaataccag cttccttctg gaatggccta caaaagcaga atgcaactga     60
aatatctttc ctaaagcaag tgtaaataga aagaacttgt gcagaaataa ctgaagaaac    120
acaggaatga tataatgcac atgctcttca tcatactcaa aaaagagaag gaacatttat    180
cataagttct cactaccaat atgatatgga ttgagacttg agcaagaata ttcatcaaaa    240
actaacaacc atataactaa agcaaatgga agcaaaaact gtcatgttac caggctactt    300
attggaagct tgcaagttgc aacaatagag gtactagcag attgaaacta gagactaagt    360
agatagattc acacatagga taatggagta cctctacctc caagccgaca caatcatnat    420
gataagatga tgggcaattg tcacaaagta ataaatcccc accatcatgg cacacagagc    480
atatcgaatc actttccaga tcagaactac tccccttcaa gcgcacatgc agtggatctc    540
tgggcnnnnn nnnacccatg aannnnncta aacactnnna tagnnacnnn nnntnnttta    600
aaaacatatg nnnnnnnnnn nnnnnngtac nnnnnncagc atgnnnnnnn nnnnnnnnna    660
cannnnnnnn nnnnttacaa cacatgnnnn nnnnnnnatc nnnnnnga                 708
```

<210> SEQ ID NO 2
<211> LENGTH: 479
<212> TYPE: DNA
<213> ORGANISM: Zea mays
<220> FEATURE:
<221> NAME/KEY: UNSURE

```
<222> LOCATION: (1)..(479)
<223> OTHER INFORMATION: n=A, T, C, or G
<220> FEATURE:
<221> NAME/KEY: unsure
<222> LOCATION: (1)..(479)
<223> OTHER INFORMATION: unsure at all n locations

<400> SEQUENCE: 2
tcaccgaggt cctgccatgg nggatatgtc gatgctgctg atctttggaa taactcattc      60
agtttcactt cctctctttg ctgctatctt ggcagaagga gccaatctca agcttataag     120
cttgtcactc ttgatgaatc aagtcagatt tnatttgcaa ggtcttttgc taactcttnc     180
taggtccagt tgaacccatt caagtcaatt ttcttgcagt tctgtggccc atcagtggta     240
tcattgatgt tcagatccag ttttgctgcc ttccgcgtca tactaaaact tcctctctca     300
cgcctgtcta gttggcctgg aggcgtcatg cttagcttgt caagaaacaa atcctctctt     360
cctctttctt tctcttgtat atcaaaggtc atgcctccta tctcctttcc tctgtgagcg     420
gaaagactga ttgacaggat atcttgatct ttctgtgagc cgtcacaggc agttaagca      479

<210> SEQ ID NO 3
<211> LENGTH: 645
<212> TYPE: DNA
<213> ORGANISM: Zea mays

<400> SEQUENCE: 3
cctgtctcct tcatcttggt cagcacaaat gcaccgacct gactcggtga gtactgcttg      60
ccatctgttg tttcaaccca agcatcacca tttggagcct tcacgatttt gtatggcacc     120
atcttcatct ctttctgtgt ctgtggatca tcaaagcgtc gcccaatcat cctctttgtt     180
ccaaagaaag tattctgggg attggttact gcctggcgct tggctggagt accaacaagt     240 ctttcacccct tctgagtaaa tgcgacaaca gatggtgttg ttctcgcacc ttcagcattc     300
tcaataactt tgggttctg cagtcattta atatagttat ttaactcagc aataaaacaa     360
atatgagaga caaaaatcat gaagggcaaa atccttatg agtaactcac ctttccttcc     420
ataacagcaa cacaagagtt agttgtcccc aaatcaatcc caataacctc atttccagca     480
gcttttgcac tgaaagcagt taccatgcaa attagcatta ctaaaatcag aaaagcgtta     540
agaactcaaa caggagataa ttattaccta aaaggtcttg caaaatttcc ccattttgag     600
catatgttgg cagcacatgt tgactgtaag ttggcaccca ggggt                     645

<210> SEQ ID NO 4
<211> LENGTH: 617
<212> TYPE: DNA
<213> ORGANISM: Zea mays
<220> FEATURE:
<221> NAME/KEY: UNSURE
<222> LOCATION: (1)..(617)
<223> OTHER INFORMATION: n=A, T, C, or G
<220> FEATURE:
<221> NAME/KEY: unsure
<222> LOCATION: (1)..(617)
<223> OTHER INFORMATION: unsure at all n locations

<400> SEQUENCE: 4
ctaactcact gccttttagn ttttttttgt tgattgtaat tgaaacaact ggacaaaaaa      60
gcatgcacat gcagagttgt gggagcgatt ctaccgttat tcctacaaac tcggacgcca     120
cgaactatat tcgccacggt ctccatggca cacaactggt caccatgcac tccgtggact     180
caggcatgca cctgaccaac tcaaaacgtg acagtaaagt aaattaacag agctgagcaa     240
caagtttatc ttctnacaac taggtctgac atacatggac cctgattttt ggacaggtta     300
```

```
acggaaacca cgaaactatg aatgtggaag gtgatttccg gtactgtgat ccgggaggct    360
ttgatgagtg catgcgcttc cttgactact tggatgaatg tgatggcaac tgggataacg    420
catttctcaa ctgggtaaat gtctgtgaaa gacggaagaa agagtatgta gctttgccta    480
atggtgactg gggtccttgg aatttcgtca aggtaaacaa gaatcttgtg ctggacactt    540
gatagacaat ctatatattc ttgtgcttct gaaatgctgg nnntccgata ttnnnannnn    600
nnnnnnnnnn nnnngct                                                   617

<210> SEQ ID NO 5
<211> LENGTH: 1184
<212> TYPE: DNA
<213> ORGANISM: Zea mays

<400> SEQUENCE: 5
gcatgtcgtc aacgccacta gctcactgcc cttcttccct tgtatcagca catgtaggta     60
acgtgataaa ccaaacataa agtacacctg cgttgccgtg tgcataaaca gcacatgttt    120
aaatctatgc tggaattcat ataccaggca aaaatgtac agtaaaaact ttacagtgat     180
aaaaggtggc acatcatgtt tccagatgat tccagcagaa aattttaggc aggccttaac    240
gcaacacatt tcgggttccc agttgttcac tgctaacctt aattttttc cagattctaa     300
ttgtacaaaa gaatatgttc tcaaaggacc aaaaaaaaac tagggttact gcaacccaaa    360
cgaatctagt cttgtccatc caaccccata agcaaataa ttggcctact ctactttcc     420
ctcggcagct atcctaacat attttaaacc taaaaaaaca tctgttaccc actcgtgcga    480
caattctcga ctgaaaacaa cttttacagc ttaactcgtg aaaccaaatg cacctcactt    540
cttaaaagag gcagcagttg ttttagttgc gctttttgc ttgagggtca tttgccacca    600
gcaccatcta tggcaatgtt ccccaactct agagccattg cctctctttc ttcactctct    660
ttcttctgct tctctgaaac accgtcacct gaattctgtg ctgagtcagg cagtgtttta    720
ggttgctgtc ggaggggacc aacatcaagc catggatgct gaagcaactg agcagctgta    780
gggcgcttct caggaacaaa atcaagtatt ggaacaagaa atccgccat cccatgagca     840
tttatttcag tgaactcata cttctccatc agcaccttgt tgagaggcca gaaccgcaag    900
cgtcggatgt gcctcaaatc cccgtaccga ttgaagaaat cacgtgagta ccgaccaccc    960
aacgcgatct gggaaacatt attcgtatac caaaattaag gacacgctga acttttttctt  1020
aaaaactatg gcaagttaaa attgaaacct tgcttacctt tcgaggcatc attcctagca   1080
gttccatcat cagtgcaagg tgatcctgca ttacaaggaa tttctcagaa ataactcca   1140
tcttgggaag ggagcaagtc aaatcattca aatttttttg caaa                    1184

<210> SEQ ID NO 6
<211> LENGTH: 685
<212> TYPE: DNA
<213> ORGANISM: Zea mays
<220> FEATURE:
<221> NAME/KEY: UNSURE
<222> LOCATION: (1)..(685)
<223> OTHER INFORMATION: n=A, T, C, or G
<220> FEATURE:
<221> NAME/KEY: unsure
<222> LOCATION: (1)..(685)
<223> OTHER INFORMATION: unsure at all n locations

<400> SEQUENCE: 6
gctcaacaat gaccactgag ggcactgaag tcgcttgatg tgctgaattg ttcgtgatgt     60
tggtggcgta ttttgtttaa ataagtaagc atggctgtga ttttatcata tnatcgatct    120
```

```
ttggggtttt atttaacaca ttgtaaaatg tgtatctatt aataactcaa tgtataagat      180
gtgttcattc ttcggttgcc atagatctgc ttatttgacc tgtgatgttt tgactccnaa      240
aaccaaaatc acaactcaat aaactcatgg aatatgtcca cctgtttctt gaagagttca      300
tctaccattc cagttggcat ttatcagtgt tgcagcggcg ctgtgctttg taacataaca      360
attgttcagg cattatatcc aaatctagag gcctaccaaa atgagataac aagccaacta      420
atctgctggg aaataggtaa caagtctcta acaagatctt aagnttattc tgagatgatg      480
tcgagaccga tgccttttgt tacgtcgtgc cgtgcctctt gttgccatgc tggtaagttg      540
ctnnnnnttg atgagggcaa gctgcttatc nnnncnnnat gannngttat nnannnnnnn      600
ntnngtgctg ctnncttggc atnnnnnnnn nnnnnnnnnc ccatctacct gcannnnnnn      660
nnnnnnnnnc nnnactgcnn nnntg                                           685

<210> SEQ ID NO 7
<211> LENGTH: 686
<212> TYPE: DNA
<213> ORGANISM: Zea mays
<220> FEATURE:
<221> NAME/KEY: UNSURE
<222> LOCATION: (1)..(686)
<223> OTHER INFORMATION: n=A, T, C, or G
<220> FEATURE:
<221> NAME/KEY: unsure
<222> LOCATION: (1)..(686)
<223> OTHER INFORMATION: unsure at all n locations

<400> SEQUENCE: 7
ttcccattcc catcaagcaa gcacattctc acttttccag catcaaggca tggagtatgg      60
caacggatga caccttgctg gataatttcc acacatacct taacatcacc aaacagcact     120
tgccatgaac tgtgagggggg attgcaaagg aagtctccta caatgataac ctgcattaca    180
ttttcataag tccccaacca ttgtagttct cggcacaggt ttgtccaaac tgataagttc     240 tttttttgttt cnttgggttc tctggactca ggcttcaagc tttcagatca aaatacttaa    300
gtattactcc tcaattctga tttctaaaag taacttgatt ttagattttg ccactcgtat     360
atatatgcag gtcattatag gattctagna acccgtcccc cattttttct tcttatgccc     420
atgctaaaca atctactaat cacagttaaa ggtcatttga atcatttcaa cacttcatta    480
atttntatgc acaagcctaa aacaacttac atttggcatc agagtatgta agtaccacat    540
gaagatatgt tttgttcaat attatgccan tagaaaagaa gaaagaagaa tgcatgttgc    600
agtaatttaa tcaagcctag taactcgtac tcatatcata cctnngtacn ntcatannnn   660
nnngctgntn ctnnnnnnnn nnnatg                                         686

<210> SEQ ID NO 8
<211> LENGTH: 441
<212> TYPE: DNA
<213> ORGANISM: Zea mays
<220> FEATURE:
<221> NAME/KEY: UNSURE
<222> LOCATION: (1)..(411)
<223> OTHER INFORMATION: n=A, T, C, or G
<220> FEATURE:
<221> NAME/KEY: unsure
<222> LOCATION: (1)..(441)
<223> OTHER INFORMATION: unsure at all n locations

<400> SEQUENCE: 8
nnnccncgta cngccangcc atacatgttt gtgtgatctt ccagaggtgt ttacaggttc      60
gaggagctgg cgttcagttt caacgggggc aaagattcaa ctgtacattc ttcctgccct    120
```

| | |
|---|---|
| cacggtcacg gccgtcggcc ggcctcntct tcttcctctt gacttgttga tttatacgct | 180 |
| cagtcacgag ggttgctaac caccgacgcg acgtcgaatn nnnnnnnnng dacaggtgct | 240 |
| gctgcatttg cttcgggccg gctactacct ccacagagca agttcaggtg gngacgtgga | 300 |
| cgacnnnagc acggtcctcc agaccgtgaa gaactgcccc atgcggacca tctacttcga | 360 |
| ggaccccgat gctttccccg aaatcgactg cttcacgtac gagacggcat cgacgtaaga | 420 |
| gcgcgtgatc tgcagtcatc a | 441 |

<210> SEQ ID NO 9
<211> LENGTH: 553
<212> TYPE: DNA
<213> ORGANISM: Zea mays

<400> SEQUENCE: 9

| | |
|---|---|
| ccggtgctgg gaaacagaag cgttgagagg gttttgaggg ggcggcggct gtgccttta | 60 |
| ctctactgta gacgggccaa aaatagaagc ccacaaataa aaccctagcc cagtaaaacc | 120 |
| tggtcagttt ctcgcctaat cggatgacta attgctctgg gtcgatgatt agttggacgc | 180 |
| caggacgacg aggacacctg gtcgggtcac cgatcctgat cgtgcccttc caggcgacct | 240 |
| agacgactaa tcgcgattag ttggatgact tgaaaacaat gtcaactacg acgttgacac | 300 |
| atctgtagca acagcatgac acttttccct ttatccgtgg tttgttttca aactgctata | 360 |
| ctacacaggt ttgtgtttag gatgctccct acatatgcat aatcatttt tagtttgtga | 420 |
| aaatgtggtg agtcaataac ttccaagtta gttgagagtc atgagaattt ttttttctg | 480 |
| aacaattgct gtcttttctt gttttagtgt aatataagat gttctcagtt atcatttttt | 540 |
| ggacatgaaa gca | 553 |

<210> SEQ ID NO 10
<211> LENGTH: 779
<212> TYPE: DNA
<213> ORGANISM: Zea mays
<220> FEATURE:
<221> NAME/KEY: UNSURE
<222> LOCATION: (1)..(779)
<223> OTHER INFORMATION: n=A, T, C, or G
<220> FEATURE:
<221> NAME/KEY: unsure
<222> LOCATION: (1)..(779)
<223> OTHER INFORMATION: unsure at all n locations

<400> SEQUENCE: 10

| | |
|---|---|
| atccccatcn ttctgcgttg gtccggtacc aggcgtaggt ccggcctcag caccaggagt | 60 |
| aggcccagca gcactggcac caggctggtt atacattgcc tggccaatct gcatcacctc | 120 |
| ctggttcaaa gcagncatgg catctttcat actctgtgtt gatccaccag aaatggcgtc | 180 |
| tttgagctcc tggagcttca catccacctt ctctttcaca ggagcgggga ctttntcgcc | 240 |
| aagctccttc agttgcttct cagtctggta gaccactgan tcngcctgnt ttttngtgtc | 300 |
| nattgcatct ctcttctctt tgtcctcctt ggcaaactta tcggcttctt ctaccattct | 360 |
| ctcaacctgc aaaaggaggt agttgttgcc ttcacgcacc aatatagaaa ttagctgaac | 420 |
| catactagtc tactacanga tcgtagaaaa taacaatgat atcacagcat cataaagtag | 480 |
| ccagcatcac atcattggca caagaatgaa acctggtaac ttgtctaacc accaaggcac | 540 |
| caacagatca ctacagttgt cagacacnng aatgctacac cgaagatttg taacatacct | 600 |
| catccttagg taacgtacta gcaccagtga tggtgatgtc ctgttctttt ccagtgccct | 660 |
| tatcaatggc agcaactgag agtatcccat ttgcatcaat atcaaacttc acttcaattt | 720 |

| | | |
|---|---|---|
| gtgggacacc acgaggtgca ggagggatcc catccaaccg gaagcttcca acggacttg | | 779 |

<210> SEQ ID NO 11
<211> LENGTH: 1131
<212> TYPE: DNA
<213> ORGANISM: Zea mays
<220> FEATURE:
<221> NAME/KEY: UNSURE
<222> LOCATION: (1)..(1131)
<223> OTHER INFORMATION: n=A, T, C, or G
<220> FEATURE:
<221> NAME/KEY: unsure
<222> LOCATION: (1)..(1131)
<223> OTHER INFORMATION: unsure at all n locations

<400> SEQUENCE: 11

| | | |
|---|---|---|
| nnngcctgca gcnnnnttca acaagaaag aaaatgatga agttttcatt aagctggtta | | 60 |
| gtttccctgt aattaatgct ttgataccttt aagtttgctg agctttgcac gggttcttcg | | 120 |
| atgttctttt gttctcgtag ggttctgaca aggataagaa gaaggaaaat gctgagcgtg | | 180 |
| atgagcgtgc caagaaggta tgcattgtag ttgcaaatca aagtagtttc tgacatatgg | | 240 |
| ttgcactgca attgcatgtg gggatggtgt gtggattgtg catgtgctag agattccgtt | | 300 |
| ttacagctct tcagcttaac actttcttat tgaatgcttg aatcagagtg gatgtagccg | | 360 |
| tagtacatct cttcagctta acactttctt cngcttatca atcttttttna gtnacaggga | | 420 |
| ctgtaatctt ataaatctta attagatctg aaattgtaag cgtgtgattt gagagttgag | | 480 |
| accaagtatt ccgaatcttc aaccttgata cacaaactct gaacaagggg aaaaagcaag | | 540 |
| gggcagtctt aatgacccat atgatctgtg tcagttccat gatgtttttg attcttatgt | | 600 |
| tatgttttg tggttaatgc ttagttgaga aaaaaaactg ggtgctnatg tgataaattat | | 660 |
| cgtaatcttg gggtgcagtc ggtgagcatc aacgagttcc tgaaacctgc tgaaggagaa | | 720 |
| aggtactacg nnggccgtgg ccgtggaagg ggccgtgggg atcgtggtgg ttttagaggc | | 780 |
| ggatacggag ggggatacag tcgtggccca gctgctgctg ctccatccat tgaagatcaa | | 840 |
| gctcagttcc caagccttgg tgggaagtga agggcgccca gctgctgctg tcaccgagcg | | 900 |
| ttgtgttgtc tgctgttgtc atatttaaat tttgtccgac gttaaatttc tgtgccacgg | | 960 |
| tttaaacgga acaaataatg atgttgcatg tggctatctt tagttatgtg gtacttgacg | | 1020 |
| ttgaataccg gagttgttgt ttatcagaat taacctccaa ttttttgtagg ccagcttta | | 1080 |
| ccattttgtt gtcttagcat gcttgcttgt ttggctgtcc tgtatggcac t | | 1131 |

<210> SEQ ID NO 12
<211> LENGTH: 728
<212> TYPE: DNA
<213> ORGANISM: Zea mays

<400> SEQUENCE: 12

| | | |
|---|---|---|
| tgctcctgcc gtcgccgtgg ctgaaatccg aatggcaatc ccagcagaag catcaaactg | | 60 |
| agcagcatga tcaaaggcgg aactcggaac ggctgctatg tatgattcga gacgtacgta | | 120 |
| cgtgatgggt tatgttgcga cgttatgaag cgtgccacgg tctgcaagag gcgaagagca | | 180 |
| gcaggtgcag gtcgcggggt gcgtccgatg cgatcccgat ctgctagctg ccgcacgtca | | 240 |
| aatcgagaat ggatctgggg tgggggggtcg gtcttcggag taacgcgacg atcgatgcat | | 300 |
| ggcacgagag cgggggggaga cgagatggcc gcgcgcgcg gcgcagtata cgtaccacga | | 360 |
| acgcgtagcc ggtgacggtg gcccaggagt tgccgagcgt ggcgccggcg aggtggacgt | | 420 |
| cgccgagctg gcccgagaac atcaccgaca ccagcgggat gccgtagtag gccatgctgg | | 480 |

```
tcagcaccat cggcaccgcg aaccccaggg atcaacagaa atggatgagt gtactgtgtg      540
tacagactac agagcagacg aaaacctgaa caagagtaag tatcacttga agcaaattta      600
acctcttaac gcatggggaa ggagacttcc atatatttct ccatcccaaa caccacgtgg      660
atgtcaataa ggcatagggt cgggttccta tgaatttctt tcaaaaatcg tcctgtccgg      720
aggagagc                                                              728
```

<210> SEQ ID NO 13
<211> LENGTH: 777
<212> TYPE: DNA
<213> ORGANISM: Zea mays
<220> FEATURE:
<221> NAME/KEY: UNSURE
<222> LOCATION: (1)..(777)
<223> OTHER INFORMATION: n=A, T, C, or G
<220> FEATURE:
<221> NAME/KEY: unsure
<222> LOCATION: (1)..(777)
<223> OTHER INFORMATION: unsure at all n locations

<400> SEQUENCE: 13

```
cctgcagctc tattttgcaa gtcgttactg acaacttgta acaaattgtt gtatttacgn       60
gcatttttac catcaaatac aatacaaaac cgcancttttt ttttngccat tgttgtattt     120
accatcaaat atgatannaa actgttgtat ttacaagcat tgttactagt catagtattc     180
cacnntntac tcatgccaat ttcagtgcta ggacttctag canctttttcc tgacnnnatg    240 ttctaattct gttccggtt tatctgcnac aggttgttga ccttgctgag attgattgca     300
atcatcctat tcttcatatg gcgtatcngg catccgcatg ccgacggaat gtggctctgg     360
tggatatcca ttgtcggaga tttctggttt ggtgtcactt ggttgctaaa ccaagttgcg     420
aagctcaacc ctaccaagcg tgtcccagac ctttccctct tgagacaaca gttcgatctc     480
cctgatggca actctaatct ccctaggctt gatgttttta tcaacaccgt cgatcccata     540
aacgagccta tgatatacac natgaactct atcctgtcca ttcttgcngt agactaccca     600
atcgatagga ctgctaccta cctctcggat gatggagggt ccataatcca ttacganngc     660
ttgcttgaga cagcaaatnt cgcgncactc tgggttccat tttnnnnnaa acatagcatt     720
gnnnnnnnnn nnnntgnnnn ntattttgct gtgaagnnnn nnnnatacac nnnnnnt       777
```

<210> SEQ ID NO 14
<211> LENGTH: 26
<212> TYPE: DNA
<213> ORGANISM: Artificial Sequence
<220> FEATURE:
<223> OTHER INFORMATION: PCR primer

<400> SEQUENCE: 14

```
tgtgcagaaa taactgaaga aacaca                                            26
```

<210> SEQ ID NO 15
<211> LENGTH: 28
<212> TYPE: DNA
<213> ORGANISM: Artificial Sequence
<220> FEATURE:
<223> OTHER INFORMATION: PCR primer

<400> SEQUENCE: 15

```
gttccttctc tttttttgagt atgatgaa                                         28
```

<210> SEQ ID NO 16
<211> LENGTH: 20

```
<212> TYPE: DNA
<213> ORGANISM: Artificial Sequence
<220> FEATURE:
<223> OTHER INFORMATION: PCR primer

<400> SEQUENCE: 16
cgatgctgct gatctttgga                                                    20

<210> SEQ ID NO 17
<211> LENGTH: 21
<212> TYPE: DNA
<213> ORGANISM: Artificial Sequence
<220> FEATURE:
<223> OTHER INFORMATION: PCR primer

<400> SEQUENCE: 17
ggctccttct gccaagatag c                                                  21

<210> SEQ ID NO 18
<211> LENGTH: 28
<212> TYPE: DNA
<213> ORGANISM: Artificial Sequence
<220> FEATURE:
<223> OTHER INFORMATION: PCR primer

<400> SEQUENCE: 18
catgcaaatt agcattacta aaatcaga                                           28

<210> SEQ ID NO 19
<211> LENGTH: 24
<212> TYPE: DNA
<213> ORGANISM: Artificial Sequence
<220> FEATURE:
<223> OTHER INFORMATION: PCR primer

<400> SEQUENCE: 19
ggaaattttg caagaccttt tagg                                               24

<210> SEQ ID NO 20
<211> LENGTH: 22
<212> TYPE: DNA
<213> ORGANISM: Artificial Sequence
<220> FEATURE:
<223> OTHER INFORMATION: PCR primer

<400> SEQUENCE: 20
ctggacaaaa aagcatgcac at                                                 22

<210> SEQ ID NO 21
<211> LENGTH: 20
<212> TYPE: DNA
<213> ORGANISM: Artificial Sequence
<220> FEATURE:
<223> OTHER INFORMATION: PCR primer

<400> SEQUENCE: 21
ggcgtccgag tttgtaggaa                                                    20

<210> SEQ ID NO 22
<211> LENGTH: 23
<212> TYPE: DNA
<213> ORGANISM: Artificial Sequence
<220> FEATURE:
<223> OTHER INFORMATION: PCR primer

<400> SEQUENCE: 22
gcttaactcg tgaaaccaaa tgc                                                23
```

<210> SEQ ID NO 23
<211> LENGTH: 20
<212> TYPE: DNA
<213> ORGANISM: Artificial Sequence
<220> FEATURE:
<223> OTHER INFORMATION: PCR primer

<400> SEQUENCE: 23
tcaagcaaaa aagcgcaact                                              20

<210> SEQ ID NO 24
<211> LENGTH: 20
<212> TYPE: DNA
<213> ORGANISM: Artificial Sequence
<220> FEATURE:
<223> OTHER INFORMATION: PCR primer

<400> SEQUENCE: 24
ggcactgaag tcgcttgatg                                              20

<210> SEQ ID NO 25
<211> LENGTH: 27
<212> TYPE: DNA
<213> ORGANISM: Artificial Sequence
<220> FEATURE:
<223> OTHER INFORMATION: PCR primer

<400> SEQUENCE: 25
cacagccatg cttacttatt taaacaa                                      27

<210> SEQ ID NO 26
<211> LENGTH: 21
<212> TYPE: DNA
<213> ORGANISM: Artificial Sequence
<220> FEATURE:
<223> OTHER INFORMATION: PCR primer

<400> SEQUENCE: 26
tggagtatgg caacggatga c                                            21

<210> SEQ ID NO 27
<211> LENGTH: 25
<212> TYPE: DNA
<213> ORGANISM: Artificial Sequence
<220> FEATURE:
<223> OTHER INFORMATION: PCR primer

<400> SEQUENCE: 27
tgctgtttgg tgatgttaag gtatg                                        25

<210> SEQ ID NO 28
<211> LENGTH: 20
<212> TYPE: DNA
<213> ORGANISM: Artificial Sequence
<220> FEATURE:
<223> OTHER INFORMATION: PCR primer

<400> SEQUENCE: 28
gacaggtgct gctgcatttg                                              20

<210> SEQ ID NO 29
<211> LENGTH: 23
<212> TYPE: DNA
<213> ORGANISM: Artificial Sequence
<220> FEATURE:
<223> OTHER INFORMATION: PCR primer

```
<400> SEQUENCE: 29
cctgaacttg ctctgtggag gta                                          23

<210> SEQ ID NO 30
<211> LENGTH: 25
<212> TYPE: DNA
<213> ORGANISM: Artificial Sequence
<220> FEATURE:
<223> OTHER INFORMATION: PCR primer

<400> SEQUENCE: 30
cgattagttg gatgacttga aaaca                                        25

<210> SEQ ID NO 31
<211> LENGTH: 23
<212> TYPE: DNA
<213> ORGANISM: Artificial Sequence
<220> FEATURE:
<223> OTHER INFORMATION: PCR primer

<400> SEQUENCE: 31
ggaaaagtgt catgctgttg cta                                          23

<210> SEQ ID NO 32
<211> LENGTH: 23
<212> TYPE: DNA
<213> ORGANISM: Artificial Sequence
<220> FEATURE:
<223> OTHER INFORMATION: PCR primer

<400> SEQUENCE: 32
cctgcaaaag gaggtagttg ttg                                          23

<210> SEQ ID NO 33
<211> LENGTH: 28
<212> TYPE: DNA
<213> ORGANISM: Artificial Sequence
<220> FEATURE:
<223> OTHER INFORMATION: PCR primer

<400> SEQUENCE: 33
gctgtgatat cattgttatt ttctacga                                     28

<210> SEQ ID NO 34
<211> LENGTH: 20
<212> TYPE: DNA
<213> ORGANISM: Artificial Sequence
<220> FEATURE:
<223> OTHER INFORMATION: PCR primer

<400> SEQUENCE: 34
gcacgggttc ttcgatgttc                                              20

<210> SEQ ID NO 35
<211> LENGTH: 27
<212> TYPE: DNA
<213> ORGANISM: Artificial Sequence
<220> FEATURE:
<223> OTHER INFORMATION: PCR primer

<400> SEQUENCE: 35
attttccttc ttcttatcct tgtcaga                                      27

<210> SEQ ID NO 36
<211> LENGTH: 21
```

```
<212> TYPE: DNA
<213> ORGANISM: Artificial Sequence
<220> FEATURE:
<223> OTHER INFORMATION: PCR primer

<400> SEQUENCE: 36
actcggaacg gctgctatgt a                                              21

<210> SEQ ID NO 37
<211> LENGTH: 22
<212> TYPE: DNA
<213> ORGANISM: Artificial Sequence
<220> FEATURE:
<223> OTHER INFORMATION: PCR primer

<400> SEQUENCE: 37
cgcttcataa cgtcgcaaca ta                                             22

<210> SEQ ID NO 38
<211> LENGTH: 21
<212> TYPE: DNA
<213> ORGANISM: Artificial Sequence
<220> FEATURE:
<223> OTHER INFORMATION: PCR primer

<400> SEQUENCE: 38
tgtggctctg gtggatatcc a                                              21

<210> SEQ ID NO 39
<211> LENGTH: 21
<212> TYPE: DNA
<213> ORGANISM: Artificial Sequence
<220> FEATURE:
<223> OTHER INFORMATION: PCR primer

<400> SEQUENCE: 39
gcttcgcaac ttggtttagc a                                              21

<210> SEQ ID NO 40
<211> LENGTH: 15
<212> TYPE: DNA
<213> ORGANISM: Artificial Sequence
<220> FEATURE:
<223> OTHER INFORMATION: probe

<400> SEQUENCE: 40
agcatgtgca ttata                                                     15

<210> SEQ ID NO 41
<211> LENGTH: 16
<212> TYPE: DNA
<213> ORGANISM: Artificial Sequence
<220> FEATURE:
<223> OTHER INFORMATION: probe

<400> SEQUENCE: 41
tgtgcatgat atcatt                                                    16

<210> SEQ ID NO 42
<211> LENGTH: 17
<212> TYPE: DNA
<213> ORGANISM: Artificial Sequence
<220> FEATURE:
<223> OTHER INFORMATION: probe

<400> SEQUENCE: 42
aggaagtgaa actgaat                                                   17
```

<210> SEQ ID NO 43
<211> LENGTH: 16
<212> TYPE: DNA
<213> ORGANISM: Artificial Sequence
<220> FEATURE:
<223> OTHER INFORMATION: probe

<400> SEQUENCE: 43
agtgaaaccg aatgag                                                     16

<210> SEQ ID NO 44
<211> LENGTH: 16
<212> TYPE: DNA
<213> ORGANISM: Artificial Sequence
<220> FEATURE:
<223> OTHER INFORMATION: probe

<400> SEQUENCE: 44
ctcctgtttg agttct                                                     16

<210> SEQ ID NO 45
<211> LENGTH: 15
<212> TYPE: DNA
<213> ORGANISM: Artificial Sequence
<220> FEATURE:
<223> OTHER INFORMATION: probe

<400> SEQUENCE: 45
tcctgcttga gttct                                                      15

<210> SEQ ID NO 46
<211> LENGTH: 13
<212> TYPE: DNA
<213> ORGANISM: Artificial Sequence
<220> FEATURE:
<223> OTHER INFORMATION: probe

<400> SEQUENCE: 46
tgggagcgat tct                                                        13

<210> SEQ ID NO 47
<211> LENGTH: 14
<212> TYPE: DNA
<213> ORGANISM: Artificial Sequence
<220> FEATURE:
<223> OTHER INFORMATION: probe

<400> SEQUENCE: 47
tgtgggagtg attc                                                       14

<210> SEQ ID NO 48
<211> LENGTH: 14
<212> TYPE: DNA
<213> ORGANISM: Artificial Sequence
<220> FEATURE:
<223> OTHER INFORMATION: probe

<400> SEQUENCE: 48
aactgctgcc tctt                                                       14

<210> SEQ ID NO 49
<211> LENGTH: 15
<212> TYPE: DNA
<213> ORGANISM: Artificial Sequence
<220> FEATURE:
<223> OTHER INFORMATION: probe

```
<400> SEQUENCE: 49
caactgctac ctctt                                                   15

<210> SEQ ID NO 50
<211> LENGTH: 15
<212> TYPE: DNA
<213> ORGANISM: Artificial Sequence
<220> FEATURE:
<223> OTHER INFORMATION: probe

<400> SEQUENCE: 50
atcacgaaca attca                                                   15

<210> SEQ ID NO 51
<211> LENGTH: 15
<212> TYPE: DNA
<213> ORGANISM: Artificial Sequence
<220> FEATURE:
<223> OTHER INFORMATION: probe

<400> SEQUENCE: 51
catcacaaac aattc                                                   15

<210> SEQ ID NO 52
<211> LENGTH: 15
<212> TYPE: DNA
<213> ORGANISM: Artificial Sequence
<220> FEATURE:
<223> OTHER INFORMATION: probe

<400> SEQUENCE: 52
accttgctgg ataat                                                   15

<210> SEQ ID NO 53
<211> LENGTH: 15
<212> TYPE: DNA
<213> ORGANISM: Artificial Sequence
<220> FEATURE:
<223> OTHER INFORMATION: probe

<400> SEQUENCE: 53
ttgctgtata atttc                                                   15

<210> SEQ ID NO 54
<211> LENGTH: 13
<212> TYPE: DNA
<213> ORGANISM: Artificial Sequence
<220> FEATURE:
<223> OTHER INFORMATION: probe

<400> SEQUENCE: 54
cttcgggccg gct                                                     13

<210> SEQ ID NO 55
<211> LENGTH: 13
<212> TYPE: DNA
<213> ORGANISM: Artificial Sequence
<220> FEATURE:
<223> OTHER INFORMATION: probe

<400> SEQUENCE: 55
ttcgggcggg cta                                                     13

<210> SEQ ID NO 56
<211> LENGTH: 15
```

```
<212> TYPE: DNA
<213> ORGANISM: Artificial Sequence
<220> FEATURE:
<223> OTHER INFORMATION: probe

<400> SEQUENCE: 56
agatgtgtca acgtc                                                  15

<210> SEQ ID NO 57
<211> LENGTH: 18
<212> TYPE: DNA
<213> ORGANISM: Artificial Sequence
<220> FEATURE:
<223> OTHER INFORMATION: probe

<400> SEQUENCE: 57
tgtgtcaaca tcgtagtt                                               18

<210> SEQ ID NO 58
<211> LENGTH: 15
<212> TYPE: DNA
<213> ORGANISM: Artificial Sequence
<220> FEATURE:
<223> OTHER INFORMATION: probe

<400> SEQUENCE: 58
cttcacgcac caata                                                  15

<210> SEQ ID NO 59
<211> LENGTH: 15
<212> TYPE: DNA
<213> ORGANISM: Artificial Sequence
<220> FEATURE:
<223> OTHER INFORMATION: probe

<400> SEQUENCE: 59
ccttcatgca ccaat                                                  15

<210> SEQ ID NO 60
<211> LENGTH: 14
<212> TYPE: DNA
<213> ORGANISM: Artificial Sequence
<220> FEATURE:
<223> OTHER INFORMATION: probe

<400> SEQUENCE: 60
ccctacgaga acaa                                                   14

<210> SEQ ID NO 61
<211> LENGTH: 16
<212> TYPE: DNA
<213> ORGANISM: Artificial Sequence
<220> FEATURE:
<223> OTHER INFORMATION: probe

<400> SEQUENCE: 61
accctaagag aacaaa                                                 16

<210> SEQ ID NO 62
<211> LENGTH: 15
<212> TYPE: DNA
<213> ORGANISM: Artificial Sequence
<220> FEATURE:
<223> OTHER INFORMATION: probe

<400> SEQUENCE: 62
acgtacgtcg aatca                                                  15
```

```
<210> SEQ ID NO 63
<211> LENGTH: 16
<212> TYPE: DNA
<213> ORGANISM: Artificial Sequence
<220> FEATURE:
<223> OTHER INFORMATION: probe

<400> SEQUENCE: 63
ccatcacgta cgtacg                                                     16

<210> SEQ ID NO 64
<211> LENGTH: 14
<212> TYPE: DNA
<213> ORGANISM: Artificial Sequence
<220> FEATURE:
<223> OTHER INFORMATION: probe

<400> SEQUENCE: 64
aaaccagaaa tctc                                                       14

<210> SEQ ID NO 65
<211> LENGTH: 14
<212> TYPE: DNA
<213> ORGANISM: Artificial Sequence
<220> FEATURE:
<223> OTHER INFORMATION: probe

<400> SEQUENCE: 65
aaccaaaaat ctcc                                                       14

<210> SEQ ID NO 66
<211> LENGTH: 35
<212> TYPE: DNA
<213> ORGANISM: Artificial Sequence
<220> FEATURE:
<223> OTHER INFORMATION: resistance allele motif

<400> SEQUENCE: 66
caggaatgat ataatgcaca tgctcttcat catac                                35

<210> SEQ ID NO 67
<211> LENGTH: 35
<212> TYPE: DNA
<213> ORGANISM: Artificial Sequence
<220> FEATURE:
<223> OTHER INFORMATION: resistance allele motif

<400> SEQUENCE: 67
tttggaataa ctcattcagt ttcacttcct ctctt                                35

<210> SEQ ID NO 68
<211> LENGTH: 35
<212> TYPE: DNA
<213> ORGANISM: Artificial Sequence
<220> FEATURE:
<223> OTHER INFORMATION: resistance allele motif

<400> SEQUENCE: 68
aagcgttaag aactcaaaca ggagataatt attac                                35

<210> SEQ ID NO 69
<211> LENGTH: 35
<212> TYPE: DNA
<213> ORGANISM: Artificial Sequence
<220> FEATURE:
<223> OTHER INFORMATION: resistance allele motif
```

<400> SEQUENCE: 69
atgcagagtt gtgggagcga ttctaccgtt attcc                             35

<210> SEQ ID NO 70
<211> LENGTH: 35
<212> TYPE: DNA
<213> ORGANISM: Artificial Sequence
<220> FEATURE:
<223> OTHER INFORMATION: resistance allele motif

<400> SEQUENCE: 70
tcacttctta aaagaggcag cagttgtttt agttg                             35

<210> SEQ ID NO 71
<211> LENGTH: 35
<212> TYPE: DNA
<213> ORGANISM: Artificial Sequence
<220> FEATURE:
<223> OTHER INFORMATION: resistance allele motif

<400> SEQUENCE: 71
tgatgtgctg aattgttcgt gatgttggtg gcgta                             35

<210> SEQ ID NO 72
<211> LENGTH: 35
<212> TYPE: DNA
<213> ORGANISM: Artificial Sequence
<220> FEATURE:
<223> OTHER INFORMATION: resistance allele motif

<400> SEQUENCE: 72
cggatgacac cttgctggat aatttccaca catac                             35

<210> SEQ ID NO 73
<211> LENGTH: 35
<212> TYPE: DNA
<213> ORGANISM: Artificial Sequence
<220> FEATURE:
<223> OTHER INFORMATION: resistance allele motif

<400> SEQUENCE: 73
ctgcatttgc ttcgggccgg ctactacctc cacag                             35

<210> SEQ ID NO 74
<211> LENGTH: 35
<212> TYPE: DNA
<213> ORGANISM: Artificial Sequence
<220> FEATURE:
<223> OTHER INFORMATION: resistance allele motif

<400> SEQUENCE: 74
aacaatgtca actacgatgt tgacacatct gtagc                             35

<210> SEQ ID NO 75
<211> LENGTH: 35
<212> TYPE: DNA
<213> ORGANISM: Artificial Sequence
<220> FEATURE:
<223> OTHER INFORMATION: resistance allele motif

<400> SEQUENCE: 75
ggtagttgtt gccttcatgc accaatatag aaatt                             35

<210> SEQ ID NO 76
<211> LENGTH: 35

```
<212> TYPE: DNA
<213> ORGANISM: Artificial Sequence
<220> FEATURE:
<223> OTHER INFORMATION: resistance allele motif

<400> SEQUENCE: 76 gatgttctttt tgttctcgta gggttctgac aagga                               35

<210> SEQ ID NO 77
<211> LENGTH: 35
<212> TYPE: DNA
<213> ORGANISM: Artificial Sequence
<220> FEATURE:
<223> OTHER INFORMATION: resistance allele motif

<400> SEQUENCE: 77
tatgtatgat tcgagacgta cgtacgtgat gggtt                                35

<210> SEQ ID NO 78
<211> LENGTH: 35
<212> TYPE: DNA
<213> ORGANISM: Artificial Sequence
<220> FEATURE:
<223> OTHER INFORMATION: resistance allele motif

<400> SEQUENCE: 78
tccattgtcg gagatttttg gtttggtgtc acttg                                35
```

RESISTANCE TO GRAY LEAF SPOT IN MAIZE

CROSS-REFERENCE TO RELATED APPLICATIONS

This application is a national phase under 35 U.S.C. §371 of International Application No. PCT/US2007/020772, which application claims priority to U.S. Provisional Application Nos. 60/847,659 (filed Sep. 28, 2006) and 60/860,210 (filed Nov. 21, 2006). These applications are incorporated herein by reference in their entirety.

INCORPORATION OF SEQUENCE LISTING

A paper copy of the Sequence Listing and a computer-readable form of the sequence listing on compact disk, containing the file named "SequenceListing.txt", which is 28,672 bytes in size (measured in Windows XP) and which was recorded on Sep. 19, 2007, are herein incorporated by reference. A paper copy of the Sequence Listing and a computer-readable form of the sequence listing, containing the file named "SequenceListing.txt", which is 28,679 bytes in size (measured in MS-DOS) and which was created on Mar. 26, 2009, are submitted herewith electronically via EFS web and are herein incorporated by reference.

FIELD OF THE INVENTION

The present invention is in the field of plant breeding and disease resistance. More specifically, the invention includes a method for breeding corn plants containing quantitative trait loci that are associated with resistance to gray leaf spot, a fungal disease associated with *Cercospora* spp. The invention further includes germplasm and the use of germplasm containing quantitative trait loci (QTL) conferring disease resistance for introgression into elite germplasm in a breeding program for resistance to gray leaf spot.

BACKGROUND OF THE INVENTION

One of the most important, yield-reducing diseases in corn is gray leaf spot (GLS), primarily caused by *Cercospora zeae-maydis* (Cz) Tehon & E.Y. Daniels (reviewed by Ward et al. 1999 Plant Dis. 83:884-895). GLS is a global problem and, in addition to prevalence in Africa, Central America and South America, it has spread across most of the U.S. cornbelt over the past 10-15 years. The fungus overwinters in field debris and requires moisture, usually in the form of heavy fogs, dews, or rains, to spread its spores and infect corn. Increasing pervasiveness has been linked to no-till practices which promote retention of fungi, such as Cz, in the soil (Paul et al. 2005 Phytopathology 95:388-396). Symptoms include a rectangular necrotic lesion which can coalesce to larger affected regions and symptoms usually appear later in the growing season. GLS in corn elicits an increased allocation of resources to damaged leaf tissue, leading to elevated risk for root and stalk rots, which ultimately results in even greater crop losses (Ward et al. 1999; Saghai-Maroof et al. 1996 Theor. Appl. Genet. 93:539-546). Yield-loss associated with GLS can be high if the symptoms are heavy and appear early, with reported losses exceeding 50% (Ward et al. 1999). Further, even if crop management strategies, such as fungicide application, are employed to reduce the incidence of Cz in the soil, there is still risk of acquiring infection from proximate fields. Notably, Cz can be readily dispersed by wind (Latterell et al. 1983 Plant Dis. 67:842-847). Thus there is a substantial need for the development of GLS resistant corn.

The introgression of disease resistance into elite germplasm has been enhanced by the advent of molecular marker-assisted breeding, which has not only dramatically increased genetic gain in agronomic traits but has also led to the identification of marker-trait associations for secondary traits. The efficacy of this approach for disease resistance breeding in maize was recently reviewed by Wisser et al. (Wisser et al. 2006 Phytopathology 96:120-129). This review also highlighted the lack of genetic resolution in many of these reports and called into question the accuracy of many historical disease resistance mapping studies due to inadequate sampling and mapping population inadequacies. In general, disease resistance mapping is difficult due to the inconsistencies of pathogen infection that can occur in field trials. In addition, the screening of materials only in summer nurseries due to regulations restricting the use of pathogens and the economics of screening for pathogens in winter nurseries make screening for disease resistance a difficult task.

Moreover, recent work has identified there are at least two sister species of Cz, as well as potentially other isolates of *Cercospora*, capable of causing GLS (Carson et al. 2006 Maydica 51:89-92; Carson et al. 2002 Plant Dis. 86:1088-109). Because different races have distinct epidemiologies, this has bearing on the methodology of GLS phenotyping used as the basis for these mapping studies, bringing into question the very nature of many so-called GLS resistance QTL.

The present invention provides and includes a method for screening and selecting a corn plant comprising QTL for GLS resistance that were derived from Brazilian mapping populations using endemic strains of Cz and single nucleotide polymorphisms (SNP) marker technology.

SUMMARY OF THE INVENTION

The present invention includes a method of introgressing an allele into a corn plant comprising (A) crossing at least one first corn plant comprising a nucleic acid sequence selected from the group consisting of SEQ ID NO: 66 to SEQ ID NO: 78 with at least one second corn plant in order to form a segregating population, (B) screening the segregating population with one or more nucleic acid markers to determine if one or more corn plants from the segregating population contains the nucleic acid sequence, and (C) selecting from the segregation population one or more corn plants comprising a nucleic acid sequence selected from the group consisting of SEQ ID NO: 66 to SEQ ID NO: 78.

The present invention includes a method of introgressing an allele into a corn plant comprising: (A) crossing at least one gray leaf spot resistant corn plant with at least one gray leaf spot sensitive corn plant in order to form a segregating population; (B) screening said segregating population with one or more nucleic acid markers to determine if one or more corn plants from said segregating population contains a gray leaf spot resistant allele, wherein said gray leaf spot resistant allele is an allele selected from the group consisting of 1, 2, 3 or 4 GLS resistant loci where one or more alleles at one or more of their loci are selected from the group consisting of GLS resistant allele 1, GLS resistant allele 2, GLS resistant allele 3, GLS resistant allele 4, GLS resistant allele 5, GLS resistant allele 5, GLS resistant allele 6, GLS resistant allele 7, GLS resistant allele 8, GLS resistance allele 9, GLS resistance allele 10, GLS resistance allele 11, GLS resistance allele 12, GLS resistance allele 13.

The present invention includes an elite corn plant comprising a nucleic acid sequence selected from the group consisting of SEQ ID NO: 66 to SEQ ID NO: 78.

The present invention includes a substantially purified nucleic acid molecule comprising a nucleic acid sequence selected from the group consisting of SEQ ID NO: 1 to SEQ ID NO: 78 and complements thereof.

The present invention includes a corn plant comprising a GLS resistant locus 1.

The present invention includes a corn plant comprising a GLS resistant locus 4.

The present invention includes a corn plant comprising GLS resistant loci 2 and 1.

The present invention includes a corn plant comprising GLS resistant loci 3 and 1.

The present invention includes a corn plant comprising GLS resistant loci 4 and 2.

The present invention includes a corn plant comprising GLS resistant loci 3 and 4.

The present invention includes a corn plant comprising GLS resistant loci 1 and 4.

The present invention includes a corn plant comprising a GLS resistant locus 1 or 4.

BRIEF DESCRIPTION OF NUCLEIC ACID SEQUENCES

SEQ ID NO: 1 is a genomic sequence derived from *Zea mays* L corresponding to GLS resistance locus 1.

SEQ ID NO: 2 is a genomic sequence derived from *Zea mays* L corresponding to GLS resistance locus 1.

SEQ ID NO: 3 is a genomic sequence derived from *Zea mays* L corresponding to GLS resistance locus 2.

SEQ ID NO: 4 is a genomic sequence derived from *Zea mays* L corresponding to GLS resistance locus 2.

SEQ ID NO: 5 is a genomic sequence derived from *Zea mays* L corresponding to GLS resistance locus 3.

SEQ ID NO: 6 is a genomic sequence derived from *Zea mays* L corresponding to GLS resistance locus 3.

SEQ ID NO: 7 is a genomic sequence derived from *Zea mays* L corresponding to GLS resistance locus 3.

SEQ ID NO: 8 is a genomic sequence derived from *Zea mays* L corresponding to GLS resistance locus 3.

SEQ ID NO: 9 is a genomic sequence derived from *Zea mays* L corresponding to GLS resistance locus 3.

SEQ ID NO: 10 is a genomic sequence derived from *Zea mays* L corresponding to GLS resistance locus 3.

SEQ ID NO: 11 is a genomic sequence derived from *Zea mays* L corresponding to GLS resistance locus 3.

SEQ ID NO: 12 is a genomic sequence derived from *Zea mays* L corresponding to GLS resistance locus 4.

SEQ ID NO: 13 is a genomic sequence derived from *Zea mays* L corresponding to GLS resistance locus 4.

SEQ ID NO: 14 is a forward PCR primer corresponding to SEQ ID NO: 1.

SEQ ID NO: 15 is a reverse PCR primer corresponding to SEQ ID NO: 1.

SEQ ID NO: 16 is a forward PCR primer corresponding to SEQ ID NO: 2.

SEQ ID NO: 17 is a reverse PCR primer corresponding to SEQ ID NO: 2.

SEQ ID NO: 18 is a forward PCR primer corresponding to SEQ ID NO: 3.

SEQ ID NO: 19 is a reverse PCR primer corresponding to SEQ ID NO: 3.

SEQ ID NO: 20 is a forward PCR primer corresponding to SEQ ID NO: 4.

SEQ ID NO: 21 is a reverse PCR primer corresponding to SEQ ID NO: 4.

SEQ ID NO: 22 is a forward PCR primer corresponding to SEQ ID NO: 5.

SEQ ID NO: 23 is a reverse PCR primer corresponding to SEQ ID NO: 5.

SEQ ID NO: 24 is a forward PCR primer corresponding to SEQ ID NO: 6.

SEQ ID NO: 25 is a reverse PCR primer corresponding to SEQ ID NO: 6.

SEQ ID NO: 26 is a forward PCR primer corresponding to SEQ ID NO: 7.

SEQ ID NO: 27 is a reverse PCR primer corresponding to SEQ ID NO: 7.

SEQ ID NO: 28 is a forward PCR primer corresponding to SEQ ID NO: 8.

SEQ ID NO: 29 is a reverse PCR primer corresponding to SEQ ID NO: 8.

SEQ ID NO: 30 is a forward PCR primer corresponding to SEQ ID NO: 9.

SEQ ID NO: 31 is a reverse PCR primer corresponding to SEQ ID NO: 9.

SEQ ID NO: 32 is a forward PCR primer corresponding to SEQ ID NO: 10.

SEQ ID NO: 33 is a reverse PCR primer corresponding to SEQ ID NO: 10.

SEQ ID NO: 34 is a forward PCR primer corresponding to SEQ ID NO: 11.

SEQ ID NO: 35 is a reverse PCR primer corresponding to SEQ ID NO: 11.

SEQ ID NO: 36 is a forward PCR primer corresponding to SEQ ID NO: 12.

SEQ ID NO: 37 is a reverse PCR primer corresponding to SEQ ID NO: 12.

SEQ ID NO: 38 is a forward PCR primer corresponding to SEQ ID NO: 13.

SEQ ID NO: 39 is a reverse PCR primer corresponding to SEQ ID NO: 13.

SEQ ID NO: 40 is a Probe 1 corresponding to the GLS resistance locus of SEQ ID NO: 1.

SEQ ID NO: 41 is a Probe 2 corresponding to the GLS resistance locus of SEQ ID NO: 1.

SEQ ID NO: 42 is a Probe 1 corresponding to the GLS resistance locus of SEQ ID NO: 2.

SEQ ID NO: 43 is a Probe 2 corresponding to the GLS resistance locus of SEQ ID NO: 2.

SEQ ID NO: 44 is a Probe 1 corresponding to the GLS resistance locus of SEQ ID NO: 3.

SEQ ID NO: 45 is a Probe 2 corresponding to the GLS resistance locus of SEQ ID NO: 3.

SEQ ID NO: 46 is a Probe 1 corresponding to the GLS resistance locus of SEQ ID NO: 4.

SEQ ID NO: 47 is a Probe 2 corresponding to the GLS resistance locus of SEQ ID NO: 4.

SEQ ID NO: 48 is a Probe 1 corresponding to the GLS resistance locus of SEQ ID NO: 5.

SEQ ID NO: 49 is a Probe 2 corresponding to the GLS resistance locus of SEQ ID NO: 5.

SEQ ID NO: 50 is a Probe 1 corresponding to the GLS resistance locus of SEQ ID NO: 6.

SEQ ID NO: 51 is a Probe 2 corresponding to the GLS resistance locus of SEQ ID NO: 6.

SEQ ID NO: 52 is a Probe 1 corresponding to the GLS resistance locus of SEQ ID NO: 7.

SEQ ID NO: 53 is a Probe 2 corresponding to the GLS resistance locus of SEQ ID NO: 7.

SEQ ID NO: 54 is a Probe 1 corresponding to the GLS resistance locus of SEQ ID NO: 8.
SEQ ID NO: 55 is a Probe 2 corresponding to the GLS resistance locus of SEQ ID NO: 8.
SEQ ID NO: 56 is a Probe 1 corresponding to the GLS resistance locus of SEQ ID NO: 9.
SEQ ID NO: 57 is a Probe 2 corresponding to the GLS resistance locus of SEQ ID NO: 9.
SEQ ID NO: 58 is a Probe 1 corresponding to the GLS resistance locus of SEQ ID NO: 10.
SEQ ID NO: 59 is a Probe 2 corresponding to the GLS resistance locus of SEQ ID NO: 10.
SEQ ID NO: 60 is a Probe 1 corresponding to the GLS resistance locus of SEQ ID NO: 11.
SEQ ID NO: 61 is a Probe 2 corresponding to the GLS resistance locus of SEQ ID NO: 11.
SEQ ID NO: 62 is a Probe 1 corresponding to the GLS resistance locus of SEQ ID NO: 12.
SEQ ID NO: 63 is a Probe 2 corresponding to the GLS resistance locus of SEQ ID NO: 12.
SEQ ID NO: 64 is a Probe 1 corresponding to the GLS resistance locus of SEQ ID NO: 13.
SEQ ID NO: 65 is a Probe 2 corresponding to the GLS resistance locus of SEQ ID NO: 13.
SEQ ID NO: 66 is a GLS resistance allele motif corresponding to SEQ ID NO: 1.
SEQ ID NO: 67 is a GLS resistance allele motif corresponding to SEQ ID NO: 2.
SEQ ID NO: 68 is a GLS resistance allele motif corresponding to SEQ ID NO: 3.
SEQ ID NO: 69 is a GLS resistance allele motif corresponding to SEQ ID NO: 4.
SEQ ID NO: 70 is a GLS resistance allele motif corresponding to SEQ ID NO: 5.
SEQ ID NO: 71 is a GLS resistance allele motif corresponding to SEQ ID NO: 6.
SEQ ID NO: 72 is a GLS resistance allele motif corresponding to SEQ ID NO: 7.
SEQ ID NO: 73 is a GLS resistance allele motif corresponding to SEQ ID NO: 8.
SEQ ID NO: 74 is a GLS resistance allele motif corresponding to SEQ ID NO: 9.
SEQ ID NO: 75 is a GLS resistance allele motif corresponding to SEQ ID NO: 10.
SEQ ID NO: 76 is a GLS resistance allele motif corresponding to SEQ ID NO: 11.
SEQ ID NO: 77 is a GLS resistance allele motif corresponding to SEQ ID NO: 12.
SEQ ID NO: 78 is a GLS resistance allele motif corresponding to SEQ ID NO: 13.

DETAILED DESCRIPTION OF THE INVENTION

The present invention provides two GLS resistance loci that are located in public bins in the maize genome that were not previously associated with GLS resistance: GLS resistance locus 1 in bin 1.03 and GLS resistance locus 4 in bin 7.04. GLS resistance locus 2, with markers falling in bins 1.06 and 1.07 and GLS resistance locus 3, with markers falling in bins 3.03 and 3.04. The present invention also provides for QTL alleles capable of conferring resistance to GLS. Alleles that are located at GLS resistance locus 1, GLS resistance locus 2, GLS resistance locus 3, and GLS resistance locus 4 are provided.

In the present invention, a GLS resistance locus 1 is located on chromosome 1. SNP markers used to monitor the introgression of GLS resistance locus 1 include those selected from the group consisting of NC0018320 and NC0105022. Illustrative GLS resistance locus 1 SNP marker DNA sequences (SEQ ID NO: 1 through 2) can be amplified using the primers indicated as SEQ ID NO: 14 through 17 with probes indicated as SEQ ID NO: 40 through 43.

In the present invention, a GLS resistance locus 2 is located on chromosome 1. SNP markers used to monitor the introgression of GLS resistance locus 2 include those selected from the group consisting of NC0109328, NC0016724, and NC0031264. These illustrative marker DNA sequences (SEQ ID NO: 3 through 5) can be amplified using the primers indicated as SEQ ID NO: 18 through 23 with probes indicated as SEQ ID NO: 44 through 49.

The present invention provides a GLS resistance locus 3, which is located on chromosome 3. Illustrative SNP markers used to monitor the introgression of GLS resistance locus 3 can be selected from the group consisting of NC0021154, NC0022590, NC0106769, NC0105291, NC0143268, and NC0071496. These illustrative marker DNA sequences (SEQ ID NO: 6 through 11) can be amplified using the primers indicated as SEQ ID NO: 24 through 35 with probes indicated as SEQ ID NO: 50 through 61.

In the present invention, a GLS resistance locus 4 is located on chromosome 7. Illustrative SNP markers that can be used to monitor the introgression of GLS resistance locus 4 are selected from the group consisting of NC0081460 and NC0015184. These illustrative marker DNA sequences (SEQ ID NO: 12 through 13) can be amplified using the primers indicated as SEQ ID NO: 36 through 39 with probes indicated as SEQ ID NO: 62 through 65.

The present invention also provides a corn plant comprising a nucleic acid sequence selected from the group consisting of SEQ ID NO: 68 to SEQ ID NO: 78 and complements thereof. The present invention also provides a corn plant comprising a nucleic acid sequence selected from the group consisting of SEQ ID NO: 1 to SEQ ID NO: 13, fragments thereof, and complements of both. The present invention also provides a corn plant comprising a nucleic acid sequence selected from the group consisting of SEQ ID NO: 14 to SEQ ID NO: 65, fragments thereof, and complements of both. In one aspect, the corn plant comprises 2, 3, 4, 5, 6, 7, 8, 9, 10, 11, 12, or 13 nucleic acid sequences selected from the group consisting of SEQ ID NO: 66 to SEQ ID NO: 78 and complements thereof. In another aspect, the corn plant comprises 2, 3, 4, 5, 6, 7, 8, 9, 10, 11, 12, or 13 nucleic acid sequences selected from the group consisting of SEQ ID NO: 1 to SEQ ID NO: 13, fragments thereof, and complements of both. In a further aspect, the corn plant comprises 2, 3, 4, 5, 6, 7, 8, 9, 10, 11, 12, or 13 nucleic acid sequences selected from the group consisting of SEQ ID NO: 14 to SEQ ID NO: 65, fragments thereof, and complements of both.

The present invention also provides a corn plant comprising 1, 2, 3 or 4 GLS resistant loci where one or more alleles at one or more of their loci are selected from the group consisting of GLS resistant allele 1, GLS resistant allele 2, GLS resistant allele 3, GLS resistant allele 4, GLS resistant allele 5, GLS resistant allele 5, GLS resistant allele 6, GLS resistant allele 7, GLS resistant allele 8, GLS resistance allele 9, GLS resistance allele 10, GLS resistance allele 11, GLS resistance allele 12, GLS resistance allele 13. In one aspect, a corn plant is provided comprising a GLS resistant allele 1. In another aspect, a corn plant is provided comprising a GLS resistant allele 4. In a further aspect, a corn plant is provided comprising GLS resistant alleles 2 and 1. In an additional aspect, a corn plant is provided comprising GLS resistant alleles 3 and 1. In an aspect, a corn plant is provided comprising GLS resistant alleles 4 and 2. In another aspect, a corn plant is provided comprising GLS resistant alleles 3 and 4. In a further aspect, a corn plant is provided comprising GLS resistant alleles 1 and 4. In an additional aspect, a corn plant is provided comprising GLS resistant alleles 1 or 4. Such alleles may be homozygous or heterozygous.

As used herein, GLS refers to any Gray Leaf Spot variant or isolate. A corn plant of the present invention can be resistant to one or more fungi capable of causing or inducing GLS. In one aspect, the present invention provides plants resistant to GLS as well as methods and compositions for screening corn plants for resistance or susceptibility to GLS, caused by the genus *Cercospora*. In a preferred aspect, the present invention provides methods and compositions for screening corn plants for resistance or susceptibility to *C. zeea-maydis*. In another aspect, the present invention provides plants resistant to and methods and compositions for screening corn plants for resistance or susceptibility to *C. zeea-maydis* strain "Type I." In a further aspect, the present invention provides plants resistant to and methods and compositions for screening corn plants for resistance or susceptibility to *C. zeea-maydis* strain "Type II." In an additional aspect, the present invention provides plants resistant to and methods and compositions for screening corn plants for resistance or susceptibility to *C. sorghi* var. *maydis*.

In an aspect, the plant is selected from the genus *Zea*. In another aspect, the plant is selected from the species *Zea mays*. In a further aspect, the plant is selected from the subspecies *Zea mays* L. ssp. *mays*. In an additional aspect, the plant is selected from the group *Zea mays* L. subsp. *mays* Indentata, otherwise known as dent corn. In another aspect, the plant is selected from the group *Zea mays* L. subsp. *mays* Indurata, otherwise known as flint corn. In an aspect, the plant is selected from the group *Zea mays* L. subsp. *mays* Saccharata, otherwise known as sweet corn. In another aspect, the plant is selected from the group *Zea mays* L. subsp. *mays* Amylacea, otherwise known as flour corn. In a further aspect, the plant is selected from the group *Zea mays* L. subsp. *mays* Everta, otherwise known as pop corn. *Zea* plants include hybrids, inbreds, partial inbreds, or members of defined or undefined populations.

Plants of the present invention can be a corn plant that is very resistant, resistant, substantially resistant, mid-resistant, comparatively resistant, partially resistant, mid-susceptible, or susceptible.

In a preferred aspect, the present invention provides a corn plant to be assayed for resistance or susceptibility to GLS by any method to determine whether a corn plant is very resistant, resistant, substantially resistant, mid-resistant, comparatively resistant, partially resistant, mid-susceptible, or susceptible.

In this aspect, a plant is assayed for GLS resistance or susceptibility by image analysis of foliar tissue using 3 leaves per plant from above the ear at a development stage between black layer and senescence, prior to death due to GLS, are captured in a digital image. The image analysis is conducted to determine the percentage of tissue damage and derive a disease rating as described in Table 1. The average of five plants per population is used. Image analysis software and methods for quantifying visual differences in two or three dimensions used are those set forth in (Bright 1987 J. Microscopy 148(pt.1):51-87; Bickmore et al. 1999 Geol. Mat. Res. 1(5):1-19).

As used herein, "substantially resistant" is less than or equal to 30% of the leaf area infected. As used herein, "partially resistant" is less than or equal to 50% of the leaf area infected. As used herein, "resistant" is between 1% and 40% of the leaf area infected. As used herein, "mid-resistant" is between 40% and 50% of the leaf area infected. As used herein, mid-susceptible is between 50% and 60% of the leaf area infected. As used herein, "susceptible" is between 60% and 100% of the leaf area infected. As used herein, "very resistant" exhibits between 0% and 5% leaf area infected.

In another aspect, the corn plant can show a comparative resistance compared to a non-resistant control corn plant. In this aspect, a control corn plant will preferably be genetically similar except for the GLS resistant allele or alleles in question. Such plants can be grown under similar conditions with equivalent or near equivalent exposure to the pathogen. In this aspect, the resistant plant or plants has less than 25%, 15%, 10%, 5%, 2% or 1% of leaf area infected.

A disease resistance QTL of the present invention may be introduced into an elite corn inbred line. An "elite line" is any line that has resulted from breeding and selection for superior agronomic performance. Examples of elite inbred lines are lines that are commercially available to farmers or corn breeders such as ZS4199, ZS02433, G3000, G1900, G0302, G1202, G2202, G4901, G3601, G1900 (Advanta Technology Ltd., Great Britain); 6TR512, 7RN401, 6RC172, 7SH382, MV7100, 3JP286, BE4207, 4VP500, 7SH385, 5X1-1755, 7SH383, 11084BM, 2JK221, 4XA321, 6RT321, BE8736, MV5125, MV8735, 3633BM (Dow, Michigan, USA); 8982-11-4-2, 8849, IT302, 9034, IT201, RR728-18, 5020, BT751-31 (FFR Cooperative, Indiana, USA); 1874WS, X532Y, 1784S, 1778S, 1880S (Harris Moran Seed Company, California, USA); FR3351, FR2108, FR3383, FR3303, FR3311, FR3361 (Illinois Foundation Seeds, Inc., Illinois, USA); NR109, JCRNR113, MR724, M42618, CI9805, JCR503, NR401, W60028, N16028, N10018, E24018, A60059, W69079, W23129 (J.C. Robinson Seed Company, Nebraska, USA); 7791, KW4773, KW7606, KW4636, KW7648, KW4U110, KWU7104, CB1, CC2 (KWS Kleinwanzlebener Saatzucgt AG, Germany); UBB3, TDC1, RAA1, VMM1, MNI1, RII1, RBO1 (Limagrain Genetics Grande Culture S.A., France); LH284, 7OLDL5, GM9215, 9OLDI1, 9OLDC2, 9OQDD1, RDBQ2, 01HG12, 79314N1, 17IN120, 17DHD7, 83IN18, 83InI14, 01INL1, LH286, ASG29, ASG07, QH111, 09DSQ1, ASG09, 86AQV2, 86ISI5, ASG25, 01DHD16, ASG26, ASG28, 90LCL6, 22DHD11, ASG17, WDHQ2, ASG27, 90DJD28, WQCD10, 17DHD5, RQAA8, LH267, 29MIF12, RQAB7, LH198Bt810, 3DHA9, LH200BT810, LH172Bt810, 011ZB2, ASG10, LH253, 861S127, 91ISI5, 22DHQ3, 911N112, 86ISI26, 011UL6, 89ADH11, 01HGI4, 161UL2, F307W, LH185Bt810, F351, LH293, LH245, 17DHD16, 90DHQ2, LH279, LH244, LH287, WDHQ11, 09DSS1, F6150, 171INI30, 4SCQ3, 01HF13, 87ATD2, 8M116, FBLL, 17QFB1, 83DNQ2, 94INK1A, NL054B, 6F545, F274, MBZA, I389972, 941NK1B, 89AHD12, I889291, 3323, 161UL6, 6077, I014738, 7180, GF6151, WQDS7, I1465837, 3327, LH176Bt810, I81664, I362697, LH310, LH320, LH295, LH254, 5750, I390186, I501150, I363128, I244225, LH246, LH247, LH322, LH289, LH283BtMON810, 85DGD1, I390185, WDDQ1, LH331 (Monsanto Co., Missouri, USA); PH1B5, PH1CA, PH0WE, PH1GG, PH0CD, PH21T, PH224, PH0V0, PH3GR, PH1NF, PH0JG, PH189, PH12J, PH1EM, PH12C, PH55C, PH3EV, PH2V7, PH4TF, PH3 KP, PH2MW, PH2N0, PH1K2, PH226, PH2VJ, PH1M8, PH1B8, PH0WD, PH3GK, PH2VK, PH1MD, PH04G, PH2KN, PH2E4, PH0DH, PH1CP, PH3P0, PH1W0, PH45A, PH2VE, PH36E, PH50P, PH8V0, PH4TV, PH2JR, PH4PV, PH3DT, PH5D6, PH9K0, PH0B3, PH2EJ, PH4TW, PH77C, PH3HH, PH8W4, PH1GD, PH1BC, PH4V6, PHOR8, PH581, PH6WR, PH5HK, PH5W4, PH0KT, PH4GP, PHJ8R, PH7CP, PH6WG, PH54H, PH5DR, PH5WB, PH7CH, PH54M, PH726, PH48V, PH3PV, PH77V, PH7JB, PH70R, PH3RC, PH6 KW, PH951, PH6ME, PH87H, PH26N, PH9AH, PH51H, PH94T, PH7AB, PH5FW, PH75K, PH8CW, PH8PG, PH5TG, PH6JM, PH3AV, PH3PG, PH6WA, PH6CF, PH76T, PH6MN, PH7BW, PH890, PH876, PHAPV, PHB5R, PH8DB, PH51K, PH87P, PH8KG, PH4CV, PH705, PH5DP, PH77N, PH86T, PHAVN, PHB6R, PH91C, PHCWK, PHC5H, PHACE, PHB6V, PH8JR, PH77P, PHBAB, PHB1V, PH3PR, PH8TN, PH5WA, PH58C, PH6HR, PH183, PH714, PHA9G, PH8BC, PHBBP, PHAKC, PHD90, PHACV, PHCEG, PHB18, PHB00, PNCND, PHCMV (Pioneer Hi-Bred International, Inc., Iowa, USA); GSC3, GSC1, GSC2, NP2138, 2227BT, ZS02234, NP2213, 2070BT, NP2010, NP2044BT, NP2073, NP2015, NP2276, NP2222, NP2052, NP2316, NP2171, WICY418C, NP2174, BX20010, BX20033, G6103, G1103, 291B, 413A, G1704 (Syngenta Participations AG, Switzerland). An elite plant is any plant from an elite line. Resistance to GLS can be provided to, for example, a hybrid plant by alleles present on either or both of the parental inbreds.

A GLS resistance QTL of the present invention may also be introduced into an elite corn plant comprising one or more transgenes conferring herbicide tolerance, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels among others. In one aspect, the herbicide tolerance is selected from the group consisting of glyphosate, dicamba, glufosinate, sulfonylurea, bromoxynil and norflurazon herbicides. These traits can be provided by methods of plant biotechnology as transgenes in corn.

A disease resistant QTL allele or alleles can be introduced from any plant that contains that allele (donor) to any recipient corn plant. In one aspect, the recipient corn plant can contain additional GLS resistant loci. In another aspect, the recipient corn plant can contain a transgene. In another aspect, while maintaining the introduced QTL, the genetic contribution of the plant providing the disease resistant QTL can be reduced by back-crossing or other suitable approaches. In one aspect, the nuclear genetic material derived from the donor material in the corn plant can be less than or about 50%, less than or about 25%, less than or about 13%, less than or about 5%, 3%, 2% or 1%, but that genetic material contains the GLS resistant locus or loci of interest.

Plants containing one or more GLS resistant loci described can be donor plants. Corn plants containing resistant loci can be, for example, screened for by using a nucleic acid molecule capable of detecting a marker polymorphism associated with resistance. In one aspect, a donor plant is SH 4802 (Budapest Treaty Deposit Number at PTA-8007). In a preferred aspect, a donor plant is the source for GLS resistance loci 2 through 4. In another aspect, a donor plant is corn inbred 32843 (Budapest Treaty Deposit Number at PTA-8006). In another preferred aspect, a donor plant is the source for GLS resistance locus 1. A donor plant can be a susceptible line. In one aspect, a donor plant can also be a recipient corn plant.

It is further understood that a corn plant of the present invention may exhibit the characteristics of any relative maturity group. In an aspect, the maturity group is selected from the group consisting of RM90-95, RM 95-100, RM 100-105, RM 105-110, RM 110-115, and RM 115-120.

An allele of a QTL can, of course, comprise multiple genes or other genetic factors even within a contiguous genomic region or linkage group, such as a haplotype. As used herein, an allele of a disease resistance locus can therefore encompass more than one gene or other genetic factor where each individual gene or genetic component is also capable of exhibiting allelic variation and where each gene or genetic factor is also capable of eliciting a phenotypic effect on the quantitative trait in question. In an aspect of the present invention the allele of a QTL comprises one or more genes or other genetic factors that are also capable of exhibiting allelic variation. The use of the term "an allele of a QTL" is thus not intended to exclude a QTL that comprises more than one gene or other genetic factor. Specifically, an "allele of a QTL" in the present in the invention can denote a haplotype within a haplotype window wherein a phenotype can be disease resistance. A haplotype window is a contiguous genomic region that can be defined, and tracked, with a set of one or more polymorphic markers wherein the polymorphisms indicate identity by descent. A haplotype within that window can be defined by the unique fingerprint of alleles at each marker. As used herein, an allele is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus. Plants of the present invention may be homozygous or heterozygous at any particular GLS locus or for a particular polymorphic marker.

The present invention also provides for parts of the plants of the present invention. Plant parts, without limitation, include seed, endosperm, ovule and pollen. In a particularly preferred aspect of the present invention, the plant part is a seed.

The present invention also provides a container of corn in which greater than 50%, 60%, 70%, 80%, 90%, 95%, or 99% of the seeds comprising 1, 2, 3 or 4 GLS resistant loci where one or more alleles at one or more of their loci are selected from the group consisting of GLS resistant allele 1, GLS resistant allele 2, GLS resistant allele 3, GLS resistant allele 4, GLS resistant allele 5, GLS resistant allele 5, GLS resistant allele 6, GLS resistant allele 7, GLS resistant allele 8, GLS resistance allele 9, GLS resistance allele 10, GLS resistance allele 11, GLS resistance allele 12, GLS resistance allele 13.

The container of corn seeds can contain any number, weight, or volume of seeds. For example, a container can contain at lest, or greater than, about 10, 25, 50, 100, 200, 300, 400, 500, 600, 700, 80, 90, 1000, 1500, 2000, 2500, 3000, 3500, 4000 or more seeds. In another aspect, a container can contain about, or greater than about, 1 gram, 5 grams, 10 grams, 15 grams, 20 grams, 25 grams, 50 grams, 100 grams, 250 grams, 500 grams, or 1000 grams of seeds. Alternatively, the container can contain at least, or greater than, about 0 ounces, 1 ounce, 5 ounces, 10 ounces, 1 pound, 2 pounds, 3 pounds, 4 pounds, 5 pounds, 10 pounds, 15 pounds, 20 pounds, 25 pounds, or 50 pounds or more seeds.

Containers of corn seeds can be any container available in the art. For example, a container can be a box, a bag, a can, a packet, a pouch, a tape roll, a pail, or a tube.

In another aspect, the seeds contained in the containers of corn seeds can be treated or untreated corn seeds. In one aspect, the seeds can be treated to improve germination, for example, by priming the seeds, or by disinfection to protect against seed-born pathogens. In another aspect, seeds can be coated with any available coating to improve, for example, plantability, seed emergence, and protection against seed-born pathogens. Seed coating can be any form of seed coating including, but not limited to, pelleting, film coating, and encrustments.

Plants or parts thereof of the present invention may also be grown in culture and regenerated. Methods for the regeneration of *Zea mays* plants from various tissue types and methods for the tissue culture of *Zea mays* are known in the art (for example, Bhaskaran et al. 1990 Crop Sci. 30:1328-1336). Regeneration techniques for plants such as *Zea mays* can use as the starting material a variety of tissue or cell types. With *Zea mays* in particular, regeneration processes have been developed that begin with certain differentiated tissue types such as meristems, (Sairam et al. 2003 Genome 46:323-3). Regeneration of mature *Zea mays* plants from tissue culture by organogenesis and embryogenesis has also been reported (Wang 1987 Plant Cell. Rep. 6:360-362; Chang 1983 Plant Cell. Rep. 2:18-185; Green et al. 1975 Crop Sci. 15:417-421). Recently, regeneration of corn from split seeds was also reported (Al-Abed et al. 2006 Planta 223:1355-1366).

The present invention also provides a disease resistant corn plant selected for by screening for disease resistance or susceptibility in the corn plant, the selection comprising interrogating genomic nucleic acids for the presence of a marker molecule that is genetically linked to an allele of a QTL associated with disease resistance in the corn plant, where the allele of a QTL is also located on a linkage group associated with disease resistant corn.

A method of introgressing an allele into a corn plant comprising (A) crossing at least one first corn plant comprising a nucleic acid sequence selected from the group consisting of SEQ ID NO: 66 to SEQ ID NO: 78 with at least one second corn plant in order to form a segregating population, (B) screening the segregating population with one or more nucleic acid markers to determine if one or more corn plants from the segregating population contains the nucleic acid sequence, and (C) selecting from the segregation population one or more corn plants comprising a nucleic acid sequence selected from the group consisting of SEQ ID NO: 66 to SEQ ID NO: 78.

The present invention also includes a method of introgressing an allele into a corn plant comprising: (A) crossing at least one gray leaf spot resistant corn plant with at least one gray leaf spot sensitive corn plant in order to form a segregating population; (B) screening the segregating population with one or more nucleic acid markers to determine if one or more corn plants from the segregating population contains a gray leaf spot resistant allele, wherein the gray leaf spot resistant allele is an allele selected from the group consisting of GLS resistant locus 1, GLS resistant locus 2, GLS resistant locus 3, and GLS resistant locus 4.

The present invention includes nucleic acid molecules. Such molecules include those nucleic acid molecules capable of detecting a polymorphism genetically or physically linked to a GLS locus. Such molecules can be referred to as markers. Additional markers can be obtained that are linked to GLS resistance locus 1, GLS resistance locus 2, GLS resistance locus 3, or GLS resistance locus 4 by available techniques. In one aspect, the nucleic acid molecule is capable of detecting the presence or absence of a marker located less than 50, 40, 30, 20, 10, 5, 2, or 1 centimorgans from a GLS. In another aspect, a marker exhibits a LOD score of 2 or greater, 3 or greater, or 4 or greater with GLS, measuring using Qgene Version 2.23 (1996) and default parameters. In another aspect, the nucleic acid molecule is capable of detecting a marker in a locus selected from the group GLS resistance locus 1, GLS resistance locus 2, GLS resistance locus 3, and GLS resistance locus 4. In a further aspect, a nucleic acid molecule is selected from the group consisting of SEQ ID NO: 1 to SEQ ID NO: 78, fragments thereof, complements thereof, and nucleic acid molecules capable of specifically hybridizing to one or more of these nucleic acid molecules.

In a preferred aspect, a nucleic acid molecule of the present invention includes those that will specifically hybridize to one or more of the nucleic acid molecules set forth in SEQ ID NO: 1 through SEQ ID NO: 78 or complements thereof or fragments of either under moderately stringent conditions, for example at about 2.0×SSC and about 65° C. In a particularly preferred aspect, a nucleic acid of the present invention will specifically hybridize to one or more of the nucleic acid molecules set forth in SEQ ID NO: 1 through SEQ ID NO: 78 or complements or fragments of either under high stringency conditions. In one aspect of the present invention, a preferred marker nucleic acid molecule of the present invention has the nucleic acid sequence set forth in SEQ ID NO: 1 through SEQ ID NO: 78 or complements thereof or fragments of either. In another aspect of the present invention, a preferred marker nucleic acid molecule of the present invention shares between 80% and 100% or 90% and 100% sequence identity with the nucleic acid sequence set forth in SEQ ID NO: 1 through SEQ ID NO: 78 or complement thereof or fragments of either. In a further aspect of the present invention, a preferred marker nucleic acid molecule of the present invention shares between 95% and 100% sequence identity with the sequence set forth in SEQ ID NO: 1 through SEQ ID NO: 78 or complement thereof or fragments of either. In a more preferred aspect of the present invention, a preferred marker nucleic acid molecule of the present invention shares between 98% and 100% sequence identity with the nucleic acid sequence set forth in SEQ ID NO: 1 through SEQ ID NO: 78 or complement thereof or fragments of either.

Nucleic acid molecules or fragments thereof are capable of specifically hybridizing to other nucleic acid molecules under certain circumstances. As used herein, two nucleic acid molecules are capable of specifically hybridizing to one another if the two molecules are capable of forming an anti-parallel, double-stranded nucleic acid structure. A nucleic acid molecule is the "complement" of another nucleic acid molecule if they exhibit complete complementarity. As used herein, molecules are exhibit "complete complementarity" when every nucleotide of one of the molecules is complementary to a nucleotide of the other. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Conventional stringency conditions are described by Sambrook et al., In: *Molecular Cloning, A Laboratory Manual*, 2nd Edition, Cold Spring Harbor Press, Cold Spring Harbor, N.Y. (1989), and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The nucleic-acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52, 9.56-9.58; Kanehisa 1984 Nucl. Acids Res. 12:203-213; and Wetmur et cd. 1968 J. Mol. Biol. 31:349-370. Appropriate stringency conditions that promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

For example, hybridization using DNA or RNA probes or primers can be performed at 65° C. in 6×SSC, 0.5% SDS, 5×Denhardt's, 100 μg/mL nonspecific DNA (e.g., sonicated salmon sperm DNA) with washing at 0.5×SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA, RNA, or cDNA fragments.

A fragment of a nucleic acid molecule can be any sized fragment and illustrative fragments include fragments of nucleic acid sequences set forth in SEQ ID NO: 1 to SEQ ID NO: 78 and complements thereof. In one aspect, a fragment can be between 15 and 25, and 30, 15 and 40, 15 and 50, 15 and 100, 20 and 25, 20 and 30, 20 and 40, 20 and 50, and 100, 25 and 30, 25 and 40, 25 and 50, 25 and 100, 30 and 40, 30 and 50, and 30 and 100. In another aspect, the fragment can be greater than 10, 15, 20, 25, 30, 35, 40, 50, 100, or 250 nucleotides.

Additional genetic markers can be used to select plants with an allele of a QTL associated with fungal disease resistance of corn of the present invention. Examples of public marker databases include, for example: Maize Genome Database, Agricultural Research Service, United States Department of Agriculture.

Genetic markers of the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

Markers, such as single sequence repeat markers (SSR), AFLP markers, RFLP markers, RAPD markers, phenotypic markers, SNPs, isozyme markers, microarray transcription profiles that are genetically linked to or correlated with alleles of a QTL of the present invention can be utilized (Walton, 1993; Burow et al. 1988). Methods to isolate such markers are known in the art.

The detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201,184; U.S. Pat. No. 4,683,202; U.S. Pat. No. 4,582,788; and U.S. Pat. No. 4,683,194), using primer pairs that are capable of hybridizing to the proximal sequences that define a polymorphism in its double-stranded form.

For the purpose of QTL mapping, the markers included should be diagnostic of origin in order for inferences to be made about subsequent populations. SNP markers are ideal for mapping because the likelihood that a particular SNP allele is derived from independent origins in the extant populations of a particular species is very low. As such, SNP markers are useful for tracking and assisting introgression of QTLs, particularly in the case of haplotypes.

The genetic linkage of additional marker molecules can be established by a gene mapping model such as, without limitation, the flanking marker model reported by Lander et al. (Lander et al. 1989 Genetics, 121:185-199), and the interval mapping, based on maximum likelihood methods described therein, and implemented in the software package MAPMAKER/QTL (Lincoln and Lander, Mapping Genes Controlling Quantitative Traits Using MAPMAKER/QTL, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander et al. (1989), and further described by Arús and Moreno-González, *Plant Breeding*, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak et al. 1995 Genetics, 139:1421-1428). Multiple regression methods or models can be also be used, in which the trait is regressed on a large number of markers (Jansen, *Biometrics in Plant Breed*, van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen et al. (Jansen et al. 1994 Genetics, 136:1447-1455) and Zeng (Zeng 1994 Genetics 136:1457-1468). Generally, the use of cofactors reduces the bias and sampling error of the estimated QTL positions (Utz and Melchinger, *Biometrics in Plant Breeding*, van Oijen, Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng 1994). These models can be extended to multi-environment experiments to analyze genotype-environment interactions (Jansen et al. 1995 Theor. Appl. Genet. 91:33-3).

Selection of appropriate mapping populations is important to map construction. The choice of an appropriate mapping population depends on the type of marker systems employed (Tanksley et al., *Molecular mapping in plant chromosomes. chromosome structure and function: Impact of new concepts* J. P. Gustafson and R. Appels (eds.). Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted× adapted).

An $F_2$ population is the first generation of selfing after the hybrid seed is produced. Usually a single $F_1$ plant is selfed to generate a population segregating for all the genes in Mendelian (1:2:1) fashion. Maximum genetic information is obtained from a completely classified $F_2$ population using a codominant marker system (Mather, Measurement of Linkage in Heredity: Methuen and Co., (1938)). In the case of dominant markers, progeny tests (e.g. $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations (e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually >$F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al. 1992 Proc. Natl. Acad. Sci. (USA) 89:1477-1481). However, as the distance between markers becomes larger (i.e., loci become more independent), the information in RIL populations decreases dramatically.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al. 1992). Information obtained from backcross populations using either codominant or dominant markers is less than that obtained from $F_2$ populations because one, rather than two, recombinant gametes are sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore et al. 1991 Proc. Natl. Acad. Sci. (U.S.A.) 88:9828-9832). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). A cultivar is a race or variety of a plant species that has been created or selected intentionally and maintained through cultivation.

Selected, non-limiting approaches for breeding the plants of the present invention are set forth below. A breeding program can be enhanced using marker assisted selection (MAS) on the progeny of any cross. It is understood that nucleic acid markers of the present invention can be used in a MAS (breeding) program. It is further understood that any commercial and non-commercial cultivars can be utilized in a breeding program. Factors such as, for example, emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred aspect, a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes.

Breeding lines can be tested and compared to appropriate standards in environments representative of the commercial target area(s) for two or more generations. The best lines are candidates for new commercial cultivars; those still deficient in traits may be used as parents to produce new populations for further selection.

The development of new elite corn hybrids requires the development and selection of elite inbred lines, the crossing of these lines and selection of superior hybrid crosses. The hybrid seed can be produced by manual crosses between selected male-fertile parents or by using male sterility systems. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Backcross breeding has been used to transfer genes for a simply inherited, highly heritable trait into a desirable homozygous cultivar or inbred line, which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have most attributes of the recurrent parent (e.g., cultivar) and, in addition, the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several reference books (Allard, "Principles of Plant Breeding," John Wiley & Sons, NY, U. of CA, Davis, Calif., 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, *In: Soybeans: Improvement, Production and Uses,* 2nd Edition, *Manograph.,* 16:249, 1987; Fehr, "Principles of variety development," *Theory and Technique,* (Vol. 1) and *Crop Species Soybean* (Vol. 2), Iowa State Univ., Macmillan Pub. Co., NY, 360-376, 1987).

An alternative to traditional QTL mapping involves achieving higher resolution by mapping haplotypes, versus individual markers (Fan et al. 2006 Genetics 172:663-686). This approach tracks blocks of DNA known as haplotypes, as defined by polymorphic markers, which are assumed to be identical by descent in the mapping population. This assumption results in a larger effective sample size, offering greater resolution of QTL. Methods for determining the statistical significance of a correlation between a phenotype and a genotype, in this case a haplotype, may be determined by any statistical test known in the art and with any accepted threshold of statistical significance being required. The application of particular methods and thresholds of significance are well with in the skill of the ordinary practitioner of the art.

It is further understood, that the present invention provides bacterial, viral, microbial, insect, mammalian and plant cells comprising the nucleic acid molecules of the present invention.

As used herein, a "nucleic acid molecule," be it a naturally occurring molecule or otherwise may be "substantially purified", if desired, referring to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic, and thus involve the capacity of the agent to mediate a chemical reaction or response.

The agents of the present invention may also be recombinant. As used herein, the term recombinant means any agent (e.g. DNA, peptide etc.), that is, or results, however indirect, from human manipulation of a nucleic acid molecule.

The agents of the present invention may be labeled with reagents that facilitate detection of the agent (e.g. fluorescent labels (Prober et al. 1987 Science 238:336-340; Albarella et al., European Patent 144914), chemical labels (Sheldon et al., U.S. Pat. No. 4,582,789; Albarella et al., U.S. Pat. No. 4,563,417), modified bases (Miyoshi et al., European Patent 119448).

Having now generally described the invention, the same will be more readily understood through reference to the following examples which are provided by way of illustration, and are not intended to be limiting of the present invention, unless specified.

EXAMPLES

Example 1

GLS Mapping Studies

In order to map putative QTL to GLS, a resistant line (SH4802; Budapest Treaty Deposit Number at PTA-8007) is crossed with a susceptible line (32843; Budapest Treaty Deposit Number at PTA-8006). For mapping, the GLS resistance phenotype (Table 1) is evaluated in 4 environments: Irai de Minas-MG (Minas Gerais, altitude: 951 m; 19° 00'S e 47°

05'W), where data are collected in the two different Brazilian planting seasons: October planting (safra) and March planting (safrinha); and in Montividiu-GO (altitude: 821 m; 17° 04'S e 51° 02'W) and Jataí-GO (Goiás, altitude: 708 m; 17° 52'S e 51° 42'W) for October planting only (safra) both locations.

TABLE 1

Description of rating scale used for GLS phenotyping.

| | Rating | Symptoms |
|---|---|---|
| Very Resistant | 1 | 0% of leaf area infected; no visible lesions |
| Very Resistant | 2 | ILA < 1%; few lesions, dispersed through lower leaves |
| Resistant | 3 | 1% ≤ ILA < 20% |
| Resistant | 4 | 20% ≤ ILA < 40% |
| Mid-Resistant | 5 | 40% ≤ ILA < 50%; lesions reaching ear leaf, with sparse lesions in the leaves above the ear |
| Mid-Susceptible | 6 | 50% ≤ ILA < 60%; lesions reaching the leaves above the ear |
| Susceptible | 7 | 60% ≤ ILA < 75% |
| Susceptible | 8 | 75% ≤ ILA < 90% |
| Susceptible | 9 | >90% of foliar area infected, with premature death of the plant before forming black layer |

ILA = infected leaf area.

These trials are planted over two years: in 2000 (safra) and 2001 (safrinha). Plots are 2 rows 5 meters long with 0.7 m between rows. Disease resistance is evaluated visually 90-95 days after planting. The infection in all experiments is natural, without artificial inoculation.

In addition to the above-described phenotyping, each population is genotyped with a combination of 126 polymorphic SNP and SSR markers. Associations between SNP marker genotype and GLS resistance phenotype (score 1-9) are evaluated and are reported in Table 2.

TABLE 2

GLS resistance loci validation using near isogenic lines (NIL) of corn. The effect in NIL is reported as the decrease in disease rating, based on the 1-9 scale in Table 1.

| Locus No. | Chromosome | Position | Marker | Variation Explained | Effects in NIL |
|---|---|---|---|---|---|
| 1 | 1 | 61.5 | Q-NC0018320 | 7.80% | −2.9 |
| 1 | 1 | 66.3 | Q-NC0105022 | | |
| 2 | 1 | 123.3 | Q-NC0109328 | 10.60% | −2 |
| 2 | 1 | 133.9 | Q-NC0016724 | | |
| 2 | 1 | 164.2 | Q-NC0031264 | | |
| 3 | 3 | 54.1 | Q-NC0021154 | 27.10% | −1.2 |
| 3 | 3 | 64 | Q-NC0022590 | | |
| 3 | 3 | 99.7 | Q-NC0071496 | | |
| 4 | 7 | 118.6 | Q-NC0081460 | 7.80% | N/A |
| 4 | 7 | 124.5 | Q-NC0015184 | | |

Table 3 lists a set of diagnostic markers for GLS resistance loci 1 through 4. SNP markers found to be in high linkage disequilibria with GLS resistance locus 1 are NC0018320 and NC0105022, indicated as SEQ ID NO: 1 through 2 (Table 3). SNP markers found to be in high linkage disequilibria with GLS resistance locus 2 are NC0109328, NC0016724, and NC0031264, indicated as SEQ ID NO: 3 through 5 (Table 3). SNP markers found to be in high linkage disequilibria with GLS resistance locus 3 are NC0021154, NC0022590, NC0106769, NC0105291, NC0143268, and NC0071496, indicated as SEQ ID NO: 6 through 11 (Table 3). SNP markers found to be in high linkage disequilibria with GLS resistance locus 4 are NC0081460 and NC0015184, indicated as SEQ ID NO: 12 through 13 (Table 3).

Also, Table 3 lists sequences for all PCR amplification primers, indicated as SEQ ID NO: 14 through 39, and probes, indicated as SEQ ID NO: 40 through 65, corresponding to these SNP markers, as well as the resistant and susceptible allele for each of the above-described bi-allelic markers. Each marker molecule contains a SNP which can be amplified using the primer pair indicated and detected using the corresponding probe pair (Table 3). Further, the resistant and susceptible alleles for each marker are designated in Table 3.

All end-point TaqMan® assays are manufactured by AB Biosystem. Reagents used for assay validation and genotyping are purchased from AB Biosystem. PCR amplification and allele calling were done according to the instruction from AB Biosystem.

TABLE 3

Listing of SNP markers for GLS resistance loci 1-4 with the resistant and susceptible allele for each marker indicated, where "*" designates a one base pair deletion.

| Marker | Chr Num | Chr Pos | GLS res. locus | SEQ ID | Res. allele | Susc. allele | SEQ ID forward primer | SEQ ID reverse primer | SEQ ID Probe 1 | SEQ ID Probe 2 | SEQ ID Res. Allele |
|---|---|---|---|---|---|---|---|---|---|---|---|
| NC0018320 | 1 | 61.5 | 1 | 1 | A | C | 14 | 15 | 40 | 41 | 66 |
| NC0105022 | 1 | 66.3 | 1 | 2 | A | G | 16 | 17 | 42 | 43 | 67 |
| NC0109328 | 1 | 123.3 | 2 | 3 | A | G | 18 | 19 | 44 | 45 | 68 |
| NC0016724 | 1 | 133.9 | 2 | 4 | C | T | 20 | 21 | 46 | 47 | 69 |
| NC0031264 | 1 | 164.2 | 2 | 5 | T | C | 22 | 23 | 48 | 49 | 70 |
| NC0021154 | 3 | 54.1 | 3 | 6 | C | T | 24 | 25 | 50 | 51 | 71 |
| NC0022590 | 3 | 64 | 3 | 7 | G | T | 26 | 27 | 52 | 53 | 72 |
| NC0106769 | 3 | 82 | 3 | 8 | C | G | 28 | 29 | 54 | 55 | 73 |
| NC0105291 | 3 | 83 | 3 | 9 | T | C | 30 | 31 | 56 | 57 | 74 |
| NC0143268 | 3 | 86 | 3 | 10 | T | C | 32 | 33 | 58 | 59 | 75 |
| NC0071496 | 3 | 99.7 | 3 | 11 | G | T | 34 | 35 | 60 | 61 | 76 |
| NC0081460 | 7 | 118.6 | 4 | 12 | ****** | GACGTA | 36 | 37 | 62 | 63 | 77 |
| NC0015184 | 7 | 124.5 | 4 | 13 | T | C | 38 | 39 | 64 | 65 | 78 |

Next, near-isogenic lines (NIL) are created for each of the putative GLS resistance loci on chromosomes 1 (2 loci) and 3 (1 locus) using corn inbred 32843 as the source for GLS resistance locus 1 and corn inbred line SH4802 as the source for GLS resistance loci 2 through 4. These are tested and validated to confirm that each region individually confers resistance (Table 2, 4). For NILs evaluation (QTL validation), trials are planted in two locations: in 2002 (October planting) at Irai de Minas-MG and Mineiros-GO (same locations described before). As above, the trials are challenged with a natural infection. Plots are one row, 3 meters long and each plot is flanked by a very susceptible line (disease multiplier). Disease resistance is evaluated at 63, 76, 92, 99, and 108 days after planting (dap) in Mineiros, and at 77, 87, 95, and 110 dap in Irai. The Area Under Disease Progress Curve (AUDPC) is correlated with all visual evaluation, and the results show a correlation of 0.98 and 0.91 between AUDPC and visual evaluation at 99 and 95 dap for Mineiros and Iraí, respectively.

TABLE 4

Average GLS scores by location and across locations for 18 NILs (n = 3 per location) derived from corn inbred lines 32843 and SH4802, with the presence (1) or absence (0) of GLS resistance loci 1-3 noted.

| | NIL | GLS score | Locus 1 | Locus 2 | Locus 3 | Average GLS score - Mineiros | Average GLS score - Iraí | Overall average GLS score |
|---|---|---|---|---|---|---|---|---|
| 1 | 3GP07024 | 7.0 | 0 | 0 | 1 | 7.0 | 7.0 | 7.0 |
| 2 | 3GP07125 | 5.0 | 0 | 0 | 1 | 5.3 | 6.7 | 6.0 |
| 3 | 3GP07054 | 4.0 | 1 | 1 | 1 | 4.3 | 5.3 | 4.8 |
| 4 | 3GP07058 | 2.5 | 1 | 1 | 1 | 3.0 | 2.0 | 2.5 |
| 5 | 3GP07076 | 6.0 | 0 | 1 | 0 | 5.3 | 6.0 | 5.7 |
| 6 | 3GP07117 | 6.0 | 0 | 1 | 0 | 6.3 | 6.3 | 6.3 |
| 7 | 3GP07034 | 4.0 | 0 | 1 | 0 | 4.7 | 5.0 | 4.8 |
| 8 | 3GP07100 | 8.0 | 0 | 0 | 0 | 7.3 | 8.0 | 7.7 |
| 9 | 3GP07056 | 7.0 | 0 | 0 | 0 | 7.0 | 7.0 | 7.0 |
| 10 | 3GP07027 | 3.0 | 0 | 1 | 1 | 3.0 | 2.3 | 2.7 |
| 11 | 3GP07062 | 3.0 | 0 | 1 | 1 | 3.7 | 3.3 | 3.5 |
| 12 | 3GP07121 | 6.0 | 1 | 1 | 0 | 6.0 | 6.7 | 6.3 |
| 13 | 23GP60PL2 | 3.0 | 1 | 1 | 0 | 3.3 | 3.3 | 3.3 |
| 14 | 3GP07008 | 6.0 | 1 | 0 | 0 | 6.0 | 6.0 | 6.0 |
| 15 | 3GP07095 | 6.0 | 1 | 0 | 0 | 5.0 | 4.0 | 4.5 |
| 16 | 23GP64PL21 | 3.0 | 1 | 0 | 0 | 3.7 | 4.0 | 3.8 |
| 17 | 3GP07063 | 4.0 | 1 | 0 | 1 | 4.3 | 3.0 | 3.7 |
| 18 | 3GP07071 | 5.0 | 1 | 0 | 1 | 5.0 | 3.3 | 4.2 |

The statistical significance of the marker-GLS resistance association for GLS resistance loci 1 through 4 was assessed using QTLCartographer (Basten et al. 1995). This analysis fits the data to the simple linear regression model:

$$y = b0 + b1x + e$$

The results give the estimates for b0, b1 and the F statistic for each marker. Whether a marker is linked to a QTL is determined by evaluating whether b1 is significantly different from zero. The F statistic compares the hypothesis H0: b1=0 to an alternative H1: b1 not 0. The pr(F) is a measure of how much support there is for H0. A smaller pr(F) indicates less support for H0 and thus more support for H1. Significance at the 5%, 1%, 0.1% and 0.01% levels are indicated by *, , * and ****, respectively. Additionally, the LOD is values are also shown in Table 5.

TABLE 5

Results of analyses for marker-GLS resistance association across 4 plantings.
The following markers for GLS resistance locus 3 were not included
in this analysis: NC0106769, NC0105291, and NC0143268.

|  | GLS res. locus | Iraí de Minas safra pr(F) | Jataí safra pr(F) | Montividiu safra pr(F) | Iraí de Minas safrinha pr(F) | Average over locations pr(F) | LOD |
| --- | --- | --- | --- | --- | --- | --- | --- |
| NC0018320 | 1 | 0.395 | 0.297 | 0.005** | 0.163 | 0.011* | 1.44 |
| NC0105022 | 1 | 0.671 | 0.223 | 0.011* | 0.154 | 0.028* | 1.06 |
| NC0109328 | 2 | 0.802 | 0.020* | 0.001** | 0.212 | 0.005** | 1.74 |
| NC0016724 | 2 | 0.954 | 0.002** | 0.002** | 0.076 | 0.002** | 2.16 |
| NC0031264 | 2 | 0.778 | 0.141 | 0.642 | 0.002** | 0.073 | 0.71 |
| NC0021154 | 3 | 0.000**** | 0.002** | 0.030* | 0.12 | 0.000*** | 3.01 |
| NC0022590 | 3 | 0.000**** | 0.000**** | 0.011* | 0.000*** | 0.000*** | 5.80 |
| NC0071496 | 3 | 0.003** | 0.001** | 0.113 | 0.478 | 0.001*** | 2.14 |
| NC0081460 | 4 | 0.001** | 0.013* | 0.169 | 0.013* | 0.000*** | 3.06 |

*$p < 0.05$;
**$p < 0.01$;
***$p < 0.001$;
****$p < 0.0001$.

What is claimed is:

1. A method of introgressing an allele into a corn plant comprising (A) crossing at least one first corn plant comprising a nucleic acid sequence selected from the group consisting of SEQ ID NOs: 66, 72, and 77 with at least one second corn plant in order to form a segregating population, (B) screening said segregating population with one or more nucleic acid markers to determine if one or more corn plants from said segregating population contain said nucleic acid sequence, and (C) selecting from said segregating population one or more corn plants comprising said nucleic acid sequence selected from the group consisting of SEQ ID NOs: 66, 72 and 77.

2. The method according to claim 1, wherein said selected one or more corn plants further comprise a second sequence selected from the group consisting of SEQ ID NOs: 66, 72, and 77.

3. The method according to claim 2, wherein said selected one or more corn plants comprise SEQ ID NOs: 66, 72 and 77.

4. The method according to claim 1, wherein said selected corn plants exhibit at least partial resistance to a gray leaf spot-inducing fungus.

5. The method according to claim 1, wherein said selected corn plants exhibit at least substantial resistance to a gray leaf spot-inducing fungus.

6. The method according to claim 5, wherein said gray leaf spot-inducing fungus is selected from the group consisting of *Cercospora zeae maydis* strain Type I and Type II.

7. The method of claim 1, wherein said one or more nucleic acid markers are linked with a SNP marker NC0018320 characterized by SEQ ID NO: 1.

8. The method of claim 7, wherein said one or more nucleic acid markers are located within 20, 10, 5, 2, or 1 centimorgans of a SNP marker NC0018320 characterized by SEQ ID NO: 1.

9. The method of claim 8, wherein said one or more nucleic acid markers are SNP marker NC0018320 characterized by SEQ ID NO: 1.

10. The method of claim 1, said screening comprises the use of a nucleic acid amplification method.

11. A method of introgressing an allele into a corn plant comprising (A) crossing at least one first corn plant comprising a nucleic acid sequence having SEQ ID NO: 66 with at least one second corn plant in order to form a segregating population, (B) screening said segregating population with one or more nucleic acid markers to determine if one or more corn plants from said segregating population contain said nucleic acid sequence, and (C) selecting from said segregating population one or more corn plants comprising said nucleic acid sequence.

12. The method of claim 11, wherein said one or more nucleic acid markers are linked with a SNP marker NC0018320 characterized by SEQ ID NO: 1.

13. A method of introgressing an allele into a corn plant comprising (A) crossing at least one first corn plant comprising said allele having a nucleic acid sequence selected from the group consisting of SEQ ID NOs: 66, 72, and 77 with at least one second corn plant in order to form a segregating population, (B) screening said segregating population with one or more nucleic acid markers to determine if one or more corn plants from said segregating population contain said allele, and (C) selecting from said segregating population one or more corn plants comprising said allele having said nucleic acid sequence selected from the group consisting of SEQ ID NOs: 66, 72, and 77.

14. The method according to claim 13, wherein said selected one or more corn plants further comprise a second sequence selected from the group consisting of SEQ ID NOs: 66, 72, and 77.

15. The method according to claim 14, wherein said selected one or more corn plants comprise SEQ ID NOs: 66, 72 and 77.

16. The method according to claim 13, wherein said selected corn plants exhibit at least partial resistance to a gray leaf spot-inducing fungus.

17. The method according to claim 13, wherein said selected corn plants exhibit at least substantial resistance to a gray leaf spot-inducing fungus.

18. The method according to claim 17, wherein said gray leaf spot-inducing fungus is selected from the group consisting of *Cercospora zeae maydis* strain Type I and Type II.

19. The method of claim 13, wherein said one or more nucleic acid markers are linked with a SNP marker NC0018320 characterized by SEQ ID NO: 1.

20. The method of claim 19, wherein said one or more nucleic acid markers are located within 20 centimorgans of a SNP marker NC0018320 characterized by SEQ ID NO: 1.

21. The method of claim 20, wherein said one or more nucleic acid markers are located within 10 centimorgans of a SNP marker NC0018320 characterized by SEQ ID NO: 1.

22. The method of claim 21, wherein said one or more nucleic acid markers are located within 5 centimorgans of a SNP marker NC0018320 characterized by SEQ ID NO: 1.

23. The method of claim 22, wherein said one or more nucleic acid markers are located within 2 centimorgans of a SNP marker NC0018320 characterized by SEQ ID NO: 1.

24. The method of claim 23, wherein said one or more nucleic acid markers are located within 1 centimorgans of a SNP marker NC0018320 characterized by SEQ ID NO: 1.

25. The method of claim 24, wherein said one or more nucleic acid markers are SNP marker NC0018320 characterized by SEQ ID NO: 1.

26. The method of claim 13, said screening comprises the use of a nucleic acid amplification method.

* * * * *

UNITED STATES PATENT AND TRADEMARK OFFICE
CERTIFICATE OF CORRECTION

| | |
|---|---|
| PATENT NO. | : 8,604,272 B2 |
| APPLICATION NO. | : 12/443162 |
| DATED | : December 10, 2013 |
| INVENTOR(S) | : David Butruille et al. |

It is certified that error appears in the above-identified patent and that said Letters Patent is hereby corrected as shown below:

In the specification

Column 10, line 49: after the words "contain at", change the word "lest" to -- least --; and Column 10, line 50: after the number "700", change the numbers "80, 90" to -- 800, 900, --.

Signed and Sealed this
Twenty-fifth Day of February, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,604,272 B2  Page 1 of 1
APPLICATION NO. : 12/443162
DATED : December 10, 2013
INVENTOR(S) : Butruille et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1231 days.

Signed and Sealed this
Twenty-second Day of September, 2015

Michelle K. Lee
*Director of the United States Patent and Trademark Office*